United States Patent [19]
Zuellig et al.

[11] Patent Number: 6,126,904
[45] Date of Patent: *Oct. 3, 2000

[54] APPARATUS AND METHODS FOR THE PREPARATION OF CHEMICAL COMPOUNDS

[75] Inventors: Marc Zuellig, Belmont, Calif.; Terry Long, Tucson, Ariz.; James Wasson, Los Altos, Calif.; Michael J. O'Neill, Pacifica, Calif.; Hung Ly, Foster City, Calif.; Bill Williams, San Francisco, Calif.; Gary S. Kath, Rahway, N.J.; Gregory W. King, Rahway, N.J.; Brian G. Uhrig, Rahway, N.J.; Steven Hutchins, Rahway, N.J.

[73] Assignee: Argonaut Technologies, Inc., San Carlos, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/925,817

[22] Filed: Sep. 5, 1997

Related U.S. Application Data

[60] Provisional application No. 60/040,050, Mar. 7, 1997.
[51] Int. Cl.[7] .............................. B01J 19/00; B01L 3/00; B01L 11/00
[52] U.S. Cl. ........................... 422/130; 422/99; 422/101; 422/129; 422/131; 422/135; 422/138
[58] Field of Search .................................. 422/99, 100, 101, 422/129, 130, 131, 138, 135

[56] References Cited

U.S. PATENT DOCUMENTS

| | | | |
|---|---|---|---|
| 4,746,490 | 5/1988 | Saneii ......................................... | 422/62 |
| 4,800,166 | 1/1989 | Horn et al. ................................. | 436/55 |
| 5,288,468 | 2/1994 | Church et al. ........................... | 435/116 |
| 5,324,483 | 6/1994 | Cody et al. ............................... | 422/131 |
| 5,352,036 | 10/1994 | Haber et al. ............................. | 366/130 |
| 5,368,823 | 11/1994 | McGraw et al. ......................... | 422/134 |
| 5,380,495 | 1/1995 | Chang et al. ............................ | 422/131 |
| 5,395,594 | 3/1995 | Nokihara et al. ........................ | 422/135 |
| 5,449,754 | 9/1995 | Nishioka .................................. | 530/334 |
| 5,453,487 | 9/1995 | Chang et al. ............................ | 530/334 |
| 5,472,672 | 12/1995 | Brennan et al. ......................... | 422/131 |
| 5,475,610 | 12/1995 | Atwood et al. .......................... | 364/500 |
| 5,503,805 | 4/1996 | Sugarman et al. ....................... | 422/131 |
| 5,541,314 | 7/1996 | McGraw et al. ..................... | 536/25.31 |
| 5,567,391 | 10/1996 | DeWitt et al. ........................... | 422/131 |
| 5,609,826 | 3/1997 | Cargill et al. .............................. | 422/99 |
| 5,614,608 | 3/1997 | Krchnak et al. ......................... | 530/334 |
| 5,627,041 | 5/1997 | Shartle ................................... | 435/7.24 |
| 5,665,975 | 9/1997 | Kedar ...................................... | 250/573 |
| 5,762,881 | 6/1998 | Haness et al. ........................... | 422/132 |
| 5,866,342 | 2/1999 | Antonenko et al. ...................... | 435/7.1 |

FOREIGN PATENT DOCUMENTS

WO 96/33010  10/1996  WIPO .............................. B01J 8/06
WO 97/14041   4/1997  WIPO ........................... G01N 35/10

*Primary Examiner*—Jill Warden
*Assistant Examiner*—Dwayne K Handy
*Attorney, Agent, or Firm*—Townsend and Townsend and Crew LLP

[57] ABSTRACT

The present invention provides apparatus and methods for the synthesis of combinatorial chemical libraries. The apparatus comprises a plurality of reaction vessels having an inner surface, an outer surface, a first opening, and a second opening. An agitator is contained within each of the reaction vessels for stimulating liquid circulation within the vessels. The apparatus has a common gas line having a plurality of gas outlet ports, where each of the reaction vessels has at least one gas outlet port positioned to feed into the vessel. The apparatus also has a common liquid line having a plurality of liquid outlet ports, where each of the reaction vessels has at least one liquid outlet port positioned to feed into the vessel. Each reaction vessel also has at least one valve coupled to the second opening on the vessel.

31 Claims, 17 Drawing Sheets

APPARATUS AND METHODS FOR THE PREPARATION OF CHEMICAL COMPOUNDS

CROSS REFERENCE TO RELATED APPLICATIONS

This application claims the benefit of U.S. Provisional Patent Application Ser. No. 60/040,050, filed on Mar. 7, 1997, the full disclosure of which is incorporated herein by reference.

BACKGROUND OF THE INVENTION

The standard method for searching for new chemical compounds which can effectively modulate biological processes employs the screening of pre-existing compounds in assays which have been designed to test particular properties of the compound being screened. Similarly, in designing compounds having desired physiochemical properties for general chemical applications, numerous compounds must be individually prepared and tested.

To reduce the time and expense involved in preparing and screening a large number of compounds for biological activity or for desirable physiochemical properties, technology has been developed for providing libraries of compounds for the discovery of lead compounds. Current methods for generating large numbers of molecularly diverse compounds focus on the use of solid phase synthesis. The generation of combinatorial libraries of chemical compounds by employing solid phase synthesis is well known in the art. For example, Geysen, et al. (*Proc. Natl. Acad. Sci. USA*, 3998 (1984) describe the construction of multi-amino acid peptide libraries; Houghton, et al. (*Nature*, 354, 84 (1991) and PCT Patent Pub. No. WO 92/09300) describe the generation and use of synthetic peptide combinatorial libraries for basic research and drug discovery; Lam, et al. (*Nature*, 354, 82 (1991) and PCT Patent Pub. No. WO 92/00091) describe a method of synthesis of linear peptides on a solid support such as polystyrene or polyacrylamide resin.

The growing importance of combinatorial chemistry as an integral component of the drug discovery process has spurred extensive technological and synthetic advances in the field (Thompson, L. A.; Ellman, J. A. (1996) *Chem. Rev.* 96,555–600). Founded in peptide synthesis devised by Merrifield, solid phase chemistry has emerged as the preeminent method for construction of small molecule combinatorial libraries (see e.g. Merrifield, R B. (I 963) *J. Am. Chem. Soc.* 85, 21492154; (a) Terrett, N. K.; Gardner, M.; Gordon, D. W.; Kobylecki, R. J.; Steele, J. (1995) *Tetrahedron* 51 (30), 8135–8173. (b) Gordon, E. M.; Barrett, R. W.; Dower, W. J.; Fodor, S. P. A.; Gallop, M. A. (1994) *J. Med Chem.* 37,1385–1401.).

Unfortunately, the generation of chemical compounds for combinatorial chemical libraries is a labor intensive process. Working with numerous reaction vessels concurrently is very difficult and time consuming. In the past, multiple solid phase reactions were conducted manually by filling a test tube with reaction media, heating it in a hot oil bath, and agitating the media a rotating magnetic stir bar. Draining was accomplished by pouring the contents of the test tube through a filter. As synthesis often required numerous steps, back and forth operation between reacting and draining procedures was physically burdensome and potentially exposed the reaction mixture to air contamination.

Although certain chemical synthesizing devices are known in the art, these devices fail to provide the qualities desired for efficiently generating large numbers of chemical compounds. There remains a need for a device which can provide heating, cooling, mixing, adding of solid reagents during synthesis, easy draining, and/or simultaneous filling of a plurality of reaction vessels in a inert atmosphere.

SUMMARY OF THE INVENTION

The present invention is directed to the synthesis of a large number of chemical compounds. In particular, the present invention expedites the synthesis process by allowing for the simultaneous introduction of chemicals into a plurality of reaction vessels. This reduces process time and physical burden on a laboratory technician or operator during a synthesis procedure. The present invention may also allow for evenly distributed heating or cooling of the reaction vessels during synthesis. In preferred embodiments, an apparatus of the present invention may further allow the operator to introduce solid reagents into the reaction vessel during processing without significant risk of contaminating the reaction vessel. The apparatus typically provides an inert atmosphere under which synthesis in the reaction vessels may occur.

In a first aspect, the present invention provides an apparatus for the synthesis of combinatorial chemical libraries. The apparatus comprises a plurality of reaction vessels having an inner surface, an outer surface, a first opening, and a second opening. An agitator is contained within each of the reaction vessels for stimulating liquid circulation within the vessels. The apparatus has a common gas line having a plurality of gas outlet ports, where each of the reaction vessels has at least one gas outlet port positioned to feed into the vessel. The apparatus also has a common liquid line having a plurality of liquid outlet ports, where each of the reaction vessels has at least one liquid outlet port positioned to feed into the vessel. Each reaction vessel also has at least one valve coupled to the second opening on the vessel.

In one embodiment, the present apparatus further comprises a support structure and a common manifold coupled to the support structure and containing the common gas line and common liquid line. A valve manifold containing a plurality of valves and a heat exchanger are also coupled to the support structure.

In another embodiment, the common manifold has a plurality of access passages where each of the passages has an outlet positioned to feed into one of said reaction vessels. Further, the common manifold may also be removably coupled to the plurality of reaction vessels. The common manifold may further have a sliding device attached to the common manifold for moving manifold between a first position and a second position. A locking device may also be provided for securing the common manifold at the first or second positions. Preferably, the common manifold has a boss for engaging the first opening on said reaction vessels, forming an air tight seal.

In a preferred embodiment, the valve manifold of the present invention has valve control means for simultaneously actuating all the valves on the manifold. Each of said valves has a liquid passageway which is preferably covered with a chemically inert material such as teflon. A heat exchanger of the present invention typically contacts the outer surface of each reaction vessel and may contain a heating element and a cooling element. Preferably, the heat exchanger has a Kapton heater or can generate a evenly distributed area of heating having a maximum temperature variance of about 3 degrees C.

The reaction vessels according to the present invention are preferably comprised of an inert material selected from the group consisting of: Teflon®, glass, propylene, polyethylene, ceramic, and stainless steel coated with Teflon®. The agitator used with the present invention may comprise a plunger, stir bar, ball, bead, column or disk made of a magnetic or ferrous material. The agitator is preferably actuated longitudinally along the inner surface of the reaction vessel by a magnet positioned externally to the reaction vessel.

In a still further embodiment, the apparatus may include a controller, a plurality of pressurized liquid containers coupled to the common liquid line, and a plurality of liquid container valves fluidly coupled to the liquid containers and the common liquid line. The controller regulates the plurality of valves to control the flow of liquids from the containers. The controller may also be used for activating the valve control means.

In an alternative embodiment, the apparatus of the present invention comprises a plurality of reaction vessels and an agitator which is actuated longitudinally along the inner surface of each of the reaction vessels. The apparatus has a common manifold which is attached to the upper opening of each of the reaction vessels, where the common manifold comprises: a gas inlet port which connects to a gas inlet line bearing a plurality of gas outlets where each gas outlet is positioned to feed into the upper opening of each of the reaction vessels; and a fluid inlet port which connects to a fluid inlet line bearing a plurality of fluid outlets where each fluid outlet is positioned to feed into the upper opening of each of the reaction vessels. The apparatus further includes a heat exchanger which contacts the outer surface of each of the reaction vessels and a vacuum system connected to the lower outlet of each of the reaction vessels.

In another aspect, the present invention provides a method for the synthesis of combinatorial chemical libraries comprising the step of providing a plurality of reaction vessels containing a reaction media. The method includes agitating the reaction media, heating the reaction media, opening a valve fluidly coupling a source of chemical with the plurality of reaction vessels, and simultaneously filling all of the reaction vessels with the chemical. A plurality of drain valves fluidly coupling the reaction vessels to a plurality of collection vessels are opened and the chemical is simultaneously drained from all of the reaction vessels to the collection vessels.

In a still further aspect, the present invention provides a method for adding reagents during the synthesis of combinatorial chemical libraries. A plurality of reaction vessels coupled to a common manifold are provided where the manifold has a gas outlet and an access passage for each of the reaction vessels. The access passage has an inlet and an outlet where the outlet of each passage is positioned to feed into one of the reaction vessels. A gas is flowed from the gas outlet to create positive gas pressure in the reaction vessel. The inlet of the access passage is opened, reagent is added, and the inlet is closed.

A further understanding of the nature and advantages of the invention may be realized by reference to the remaining portions of the specification and the drawings.

DESCRIPTION OF THE PREFERRED EMBODIMENT

I. Introduction

Figure 1A:
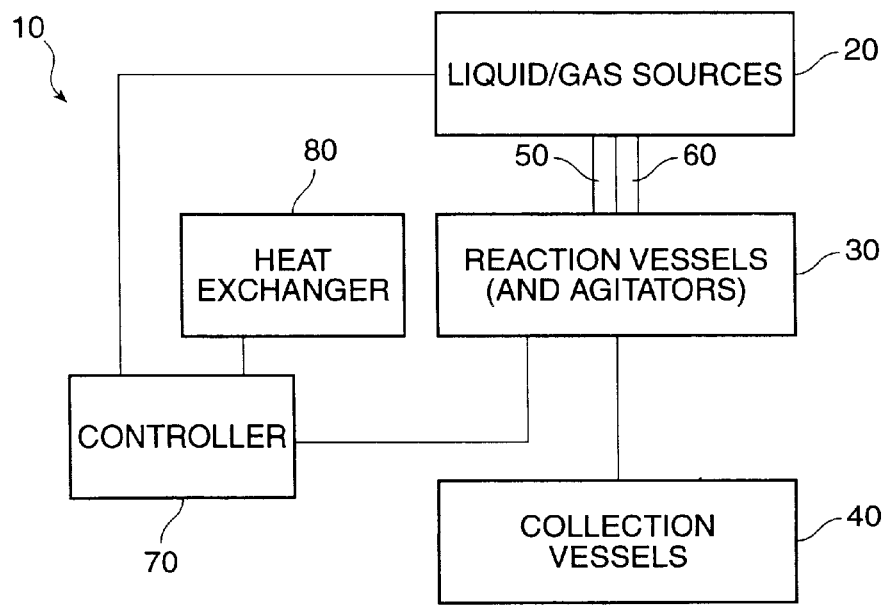
FIG. 1A is a simplified schematic diagram of one embodiment of the present invention.

The present invention is directed to the synthesis of chemical compounds, such as for the generation of combinatorial chemical libraries. Specifically, the present invention provides an apparatus by which any variety of single compounds or combinatorial libraries may be created. The reaction apparatus of the present invention provides numerous advantages over known instrumentation. With large numbers of samples to process, the present apparatus facilitates the synthesis by allowing for common introduction of reagents and the simultaneous washing of an array of reaction vessels. This may be performed under an inert atmosphere over the reaction chambers. The present invention may also provide an agitator for uniformly and gently mixing the reaction media. Constant and evenly distributed heating and cooling may be provided during synthesis.

Although the present invention may be manually controlled by the operator, to facilitate the ease of operation, certain functions in the apparatus, such as agitation of the reaction mixture, heating and cooling of the reaction vessel, inlet of inert atmosphere, introduction of reagents and solvents, rinsing and draining of reaction mixtures, and the like may be conducted by robotic automation or computer control. Accordingly, certain embodiments of the present invention are directed to the use of the apparatus which is partially or entirely conducted by robotic automation or under computer control.

As will be readily apparent to one skilled in the art the present invention is useful for the solid phase synthesis of organic compounds, including peptides. This device may be used for both solid phase chemistry and liquid-liquid chemistry, but solid phase chemistry is preferred. Alternatively, the present invention may be employed for the synthesis of organic compounds in the solution phase.

For the synthesis of compounds, appropriate starting materials may be attached to a support. Preferred support materials include solid polymeric materials, such as polyacrylamide, polydextran, polyethylene glycol, polystyrene, cellulose, sephadex, resins, combinations thereof, and the like. Alternate support materials include glass, acrylic, latex, and ceramics. Synthetic reactions may be conducted on the support-bound starting materials to obtain the desired compounds which may then be cleaved from the support.

The present invention may be employed in essentially any synthetic reaction. Thus, the present invention is useful in almost all of the synthetic reactions which are known to one of skill in the art, including, for example, peptide synthesis, acylation, alkylation, condensation, cyclization, halogenation, heterogeneous catalysis, hydrolysis, metallation, nitration, nucleophilic displacement, organometallic reactions, oxidation, reduction, sulfonation, acid chloride formation, Diels-Alder reaction, Friedel-Crafts reactions, Fischer indole synthesis, Michael reactions, and the like (see e.g., H. O. House, "Modem Synthetic Reactions", 2nd ed. (Benjamin/Cummings, Menlo Park 1972); J. March, "Advanced Organic Chemistry", 3rd ed., (John Wiley & Sons, New York, 1985); Fieser and Fieser, "Reagents for Organic Synthesis", Volumes lend (Wiley Interscience, New York)). Likewise, the present invention has application in essentially any synthetic reaction which may be conducted in solution or on solid phase supports, including acetal formation, alkylations, alkynation, chiral alkylation, reductive alkylation, carbanion reactions, Grignard reactions, organocadmium/manganese reactions, organolidiim reactions, organozinc reactions, carbene insertion, condensations, Claisen reactions, aldol reactions, Dieckmann cyclization, Knoevenagel condensations, mannich reactions, cycloadditions, cyclizations (in particular to form heterocyclic rings), Friedel-Crafbs reactions, halogenation, bromination, chlorination, nucleophilic addition, Michael addition, aromatic nucleophilic substitution, Finkelstein reaction, Mitsunobu reaction, palladium (0) catalyzed reactions, Stille coupling, Suzuki coupling, Heck reaction, carbamate/urea formation, oxidation of primary alcohol to aldehyde, Sharpless reaction, oxidation of secondary alcohol to ketone, oxidation of aldehyde to carboxylic acid, epoxidation, oxidation of primary chloride to aldehyde, oxidative phenol coupling, reduction of acid to alcohol, reduction of aldehyde to alcohol, reduction of alkyne to alkene, reduction of amide to amine, reduction of aryl nitro to amine, reduction of azide to amine, reduction of ester to alcohol, reduction of imine to amine, reduction of iodide to alkyl, reduction of ketone to alcohol, Wittig reaction, Homer-Emmons condensation, and the like (see generally, "Solid Phase Organic Chemistry (SPOC)" and "Solid Phase Inorganic Chemistry (SPIC)", Chiron Mimotopes, pp. 1–31 (August 1995).

The term "combinatorial library" as used herein refers to a collection of compounds in which the compounds comprising the collection are composed of one or more subunits or monomeric units (i.e. synthons). The subunits may be selected from natural or unnatural moieties including amino acids, nucleotides, sugars, lipids, carbohydrates, dienes, dienopholes, and the like. The compounds of the combinatorial library differ in one or more ways with respect to the type(s), number, order or modification of the subunits comprising the compounds.

Combinatorial libraries generated by the methods of the present invention may be screened for pharmacologically or diagnostically useful compounds, as well as for desired physical or chemical properties. It will be clear to one skilled in the art that such screening may be conducted on a library of compounds which have been separated from the polyvalent support, or may be conducted directly on the library of compounds which are still linked to the polyvalent support.

The term "line" as used herein, with regards to a common liquid line and a common gas line, refers to a fluid conduit which may be in the form of a channel created in a block of material or as a separate, stand-alone entity such as a pipe or a tube. The term is intended to describe a variety of different fluid conduits.

A. Overview of Apparatus

Referring first to FIG. 1A, an apparatus 10 for the synthesis of combinatorial chemical libraries is depicted in a simplified schematic diagram. The apparatus 10 comprises liquid or gas sources fluidly coupled to a plurality of reaction vessels 30 which release into a plurality of collection vessels 40. A common liquid line 50 and/or a common gas line 60 provide liquid and/or gas to the plurality of reaction vessels 30, respectively. It should be understood that a variety of different devices as discussed below may be used to fluidly couple the source 20 to the reaction vessel 30 so long as a common liquid line 50 and preferably a common gas line 60 are fluidly coupled to the plurality of reaction vessels 30.

A controller 70 is typically used to regulate the flow of material from the liquid and/or gas sources 20 to the reaction vessels 30. The controller 70 may also be used control the ramp time, heating cycle, and other variables associated with the heat exchanger 80 in order to facilitate reactions in the vessels 30. Agitation of the reaction vessels 30 and release of material from reaction vessels 30 to the collection vessels 40, may also be regulated by the controller 70. Advantageously, the present invention has a common liquid line 50 and a common gas line 60 which facilitate simultaneous filling or flushing of the reaction vessels 30. This is particularly useful when large numbers of chemical compounds are to be synthesized. The controller 70 may further facilitate the chemical synthesis by automating the various heating and fluid transfer procedures which occur. Although preferably remaining under the automated control of controller 70, the heater and other devices coupled to controller 70 may be manually operated as desired during the course of chemical synthesis.

B. Reaction Vessel

Figure 1B:
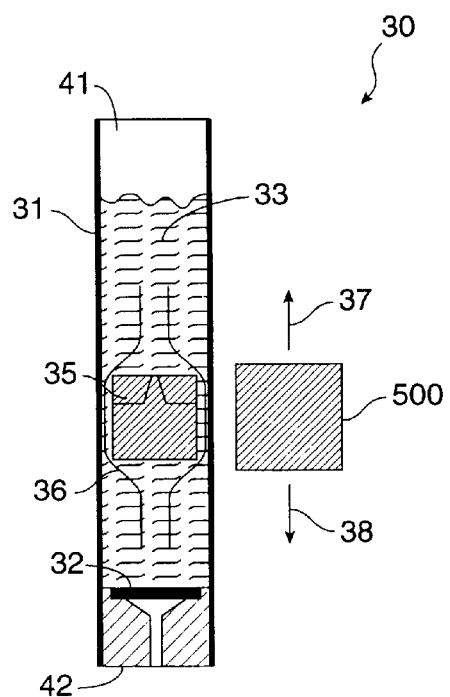
FIG. 1B shows a cross-sectional view of a reaction vessel according to a preferred embodiment of the present invention.

Referring now to FIG. 1B, a diagrammatic cross-sectional side view of a reaction vessel 30 according to a preferred embodiment is shown. Although size and shape may vary, the general features of the reaction vessel 30 are common to various embodiments of apparatus 10. The reaction vessel 30 typically comprises a linear body 31 which is made of Teflon®, glass, propylene, polyethylene, quartz, ceramic, stainless steel coated with Teflon®, or other inert material able to withstand the temperature, pressure, and chemical environment to which the reaction vessel 30 is exposed. The reaction vessel 30 has a first opening 41 and a second opening 42 to permit the introduction and removal of reagents. A typical reaction vessels 30 may be sized between about 15 ml to 45 ml. Of course, the apparatus 10 may be adjusted to accommodate reaction vessels 30 of other sizes. Preferably, the composition of the reaction vessel permits the visualization of its contents by being transparent or translucent.

For ease of manufacture and to facilitate conducting chemical reactions, it is preferred that each linear reaction vessel be cylindrical in shape. However, other shapes such as rectangular, hexagonal or prismatic may be beneficial to certain applications of the reaction vessel 30. To facilitate manipulations such as washing of resin and removal of solvents or cleaved products, it is preferred that linear reaction vessels be situated in the chemical synthesizer in a vertical or essentially vertical orientation, however, the instant invention contemplates other orientations of the linear reaction vessels which are not vertical, up to and including horizontal orientations.

In a preferred embodiment, the reaction vessel is comprised of Teflon® tubing. Teflon® tubing is generally low cost and can be cut to different lengths to accommodate different volumes of fluid. The Teflon® tubing is preferably transparent or translucent to facilitate observation of the disposition of the contents of the reaction vessel. Teflon® tubing also has advantages in that there is minimal resin sticking and that they readily conform to the heater/cooler block for better thermal transfer. Due to the low cost and deformation which may occur to the reaction vessel 30, the reaction vessels are typically consumable items which are disposed of after one usage. In an alternate embodiment, the reaction vessel may be a solid phase cartridge or a syringe barrel.

The reaction vessel 30 is generally linear in shape and contains a frit 32 in the lower portion of the vessel. The frit 32 may also be designed to fit over a protrusion or boss 400 used in the apparatus 10. The frit 32 preferably supports a quantity of a synthesis support such as a solid phase resin (not shown) during draining operations. The frit 32 is comprised of an inert material, such as Teflon®, sintered glass, sintered metal, glass wool or ceramic, and is of a porosity appropriate to the type of solid support being employed. For example, in the most preferred embodiment, the frit 32 is a Teflon® frit with a 25 micron pore size. In operation the reaction vessel 30 contains reaction media 33 and preferably operates under an atmosphere of inert gas. The inert atmosphere may be necessary as certain chemical processes use chemical reagents which are reactive with molecular oxygen, water vapor, or other agents commonly found in air.

As shown in FIG. 1B, a preferred embodiment of reaction vessel 30 includes an agitator 35. Flow of the reaction media 33 around the agitator 35 is illustrated by the depiction of flow lines 36. In a preferred embodiment of the agitator 35, the longitudinally actuated agitator 35 is a magnetic or ferrous plunger, stir bar, ban, bead, column, disk and the like which moves longitudinally back and forth along the inner surface of the reaction vessel 30 under the force of a magnet 500 (FIG. 14) positioned externally to the reaction vessel. The agitator 35 fits loosely in the reaction vessel 30 so that when the agitator 35 is moved longitudinally (i.e. in the directions depicted by arrows 37 and 38) along the inner surface of the reaction vessel 30, the reaction media 33 streams around the agitator 35 causing a gentle mixing action.

Figure 1C:
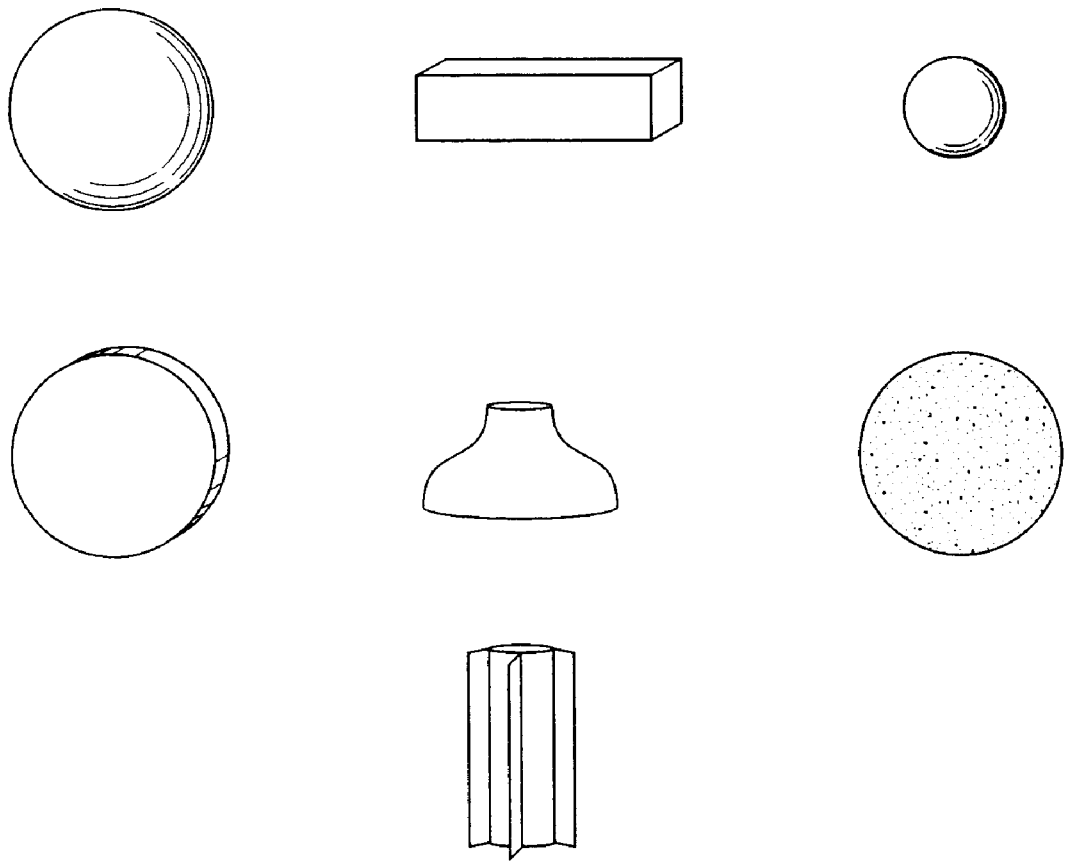
FIG. 1C depicts a variety of different embodiments for an agitator of the present invention.

Preferably the agitator 35 is coated with an inert material such as Teflon®, glass or ceramic to provide for chemical resistance. Optionally, the agitator 35 may be perforated or may possess surface modifications such as grooves, dimples, vanes, texturing and the like to increase the efficiency of mixing (FIG. 1C). The externally positioned magnet may be moved, for example, by an electric motor, or a hydraulic or pneumatic piston. Preferably, the frequency of motion of the externally positioned magnet 500 (FIG. 14) may be adjusted to provide for an appropriate frequency and stroke (i.e. distance of linear travel) of mixing. In an even more preferred embodiment, agitation or mixing of the reaction media is accomplished by employing an agitator 35 which comprises a cylindrically shaped Teflon® plunger bearing a permanent magnetic encapsulated inside it.

II. Preferred Embodiment of the Apparatus

Figure 2:
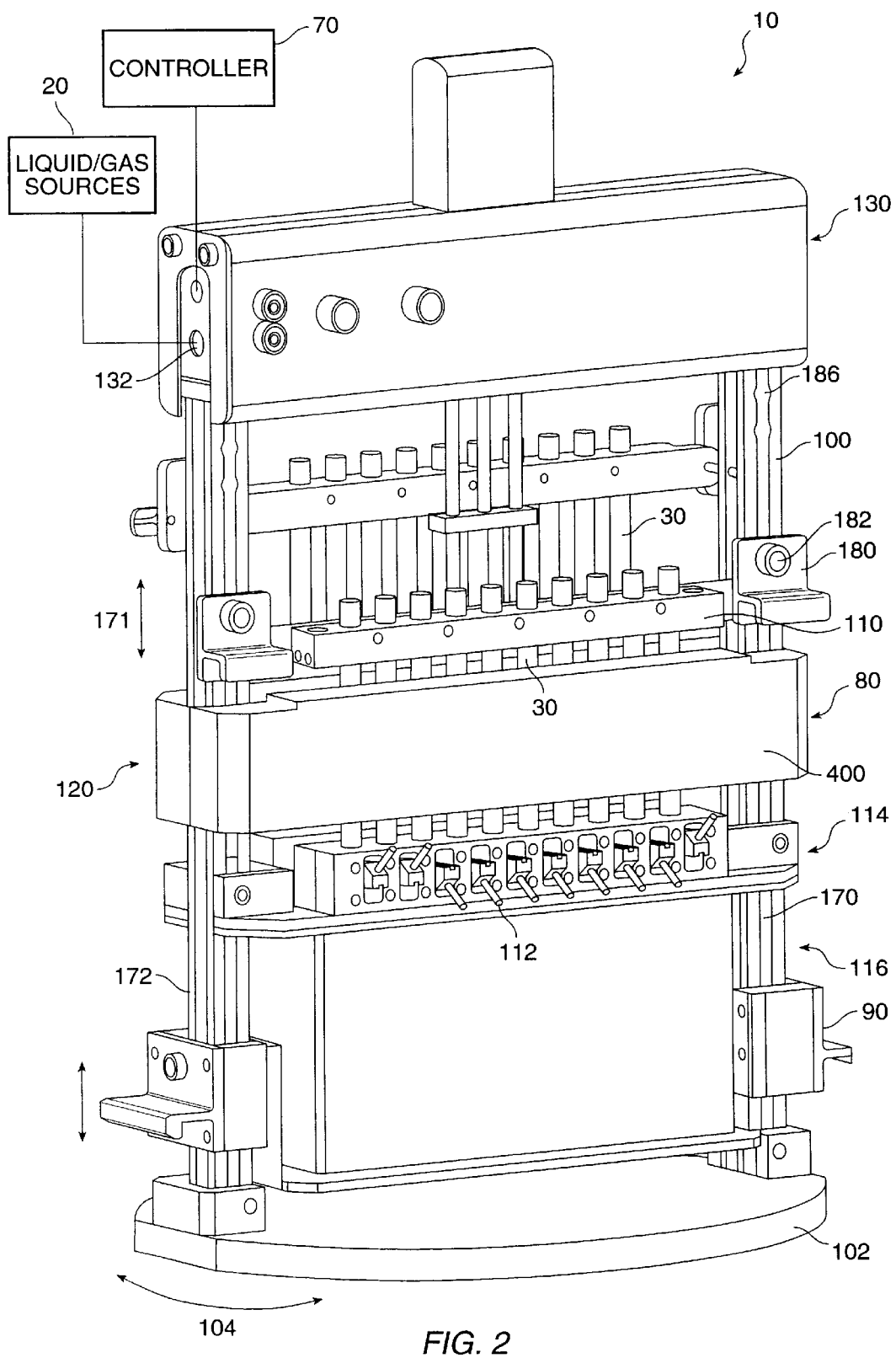
FIG. 2 is a perspective view of a preferred embodiment of the apparatus of the present invention.

Referring now to FIGS. 2 through 15, a preferred embodiment of an apparatus 10 for the synthesis of combinatorial chemical libraries will now be described. FIG. 2 shows a support structure 100 attached to a rotatable base 102. An operator may rotate the base 102 about its center axis, as shown by arrows 104, so as to provide access to components on both sides of the support structure 100. This feature is particularly desirable in a crowded laboratory or manufacturing environment where space is at a minimum. The support structure 100 is preferably made from material, such as aluminum or stainless steel, to provide a stable frame on which other components of the apparatus 10 may be mounted.

Figure 15:
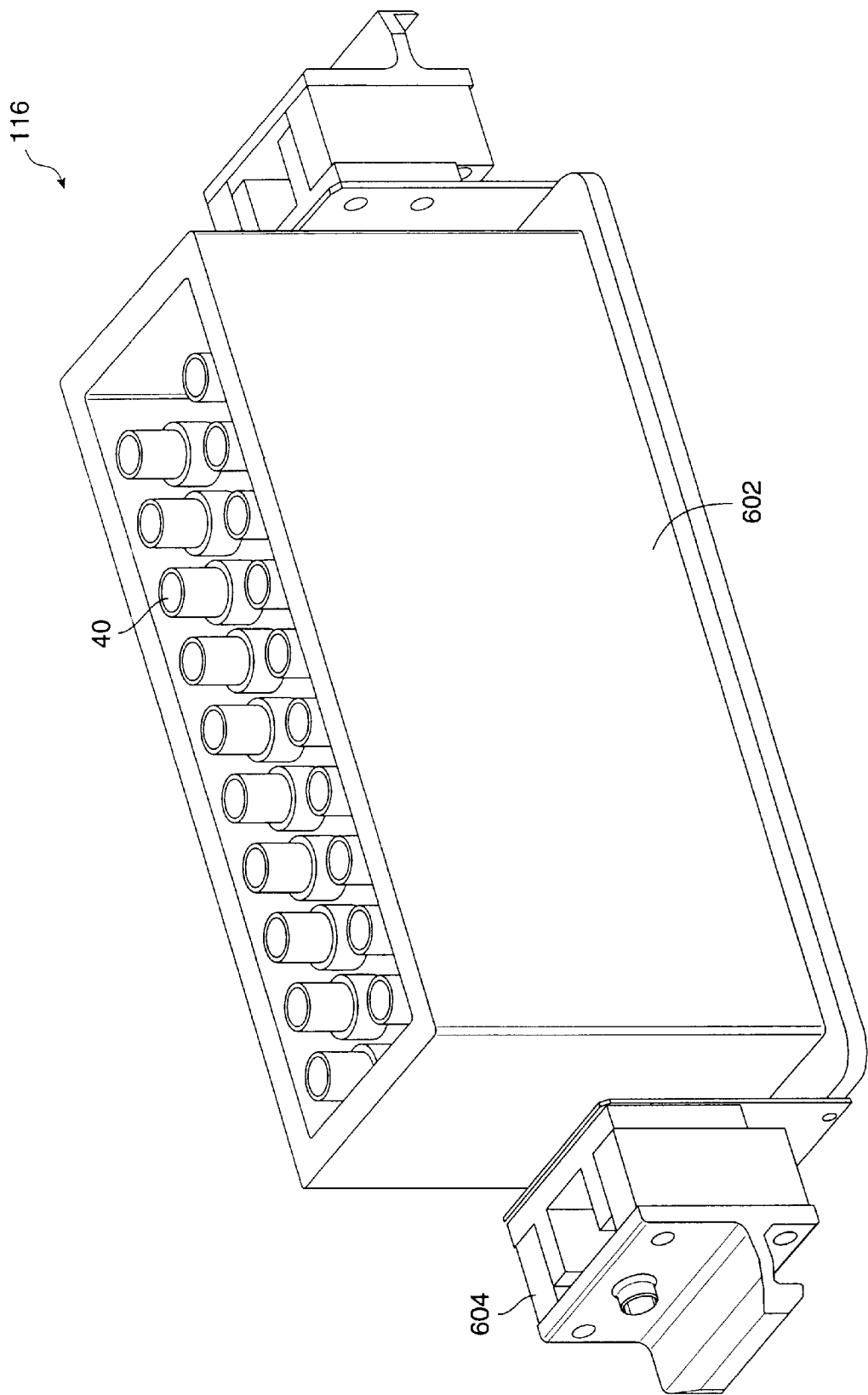
FIG. 15 is a perspective view of a preferred embodiment of the collector.

The embodiment of apparatus 10 shown in FIG. 2 comprises a plurality of reaction vessels 30 coupled to a common manifold 110, a plurality of valves 112 on a valve manifold 114, and a collector 116 which contains a plurality of collection vessels 40 (FIG. 15). The apparatus 10 also comprises a heat exchanger 80 and an upper housing 130. Liquid and gas sources 20 are fluidly coupled to the upper housing 130 through housing port 132. The fluids entering through housing port 132 are transported along the support structure 100 by conduits or other devices known in the art to the common manifold 110. Common manifold 110 contains the common liquid line 50 and common gas line 60 which are fluidly coupled to the reaction vessels 30.

Figure 3:
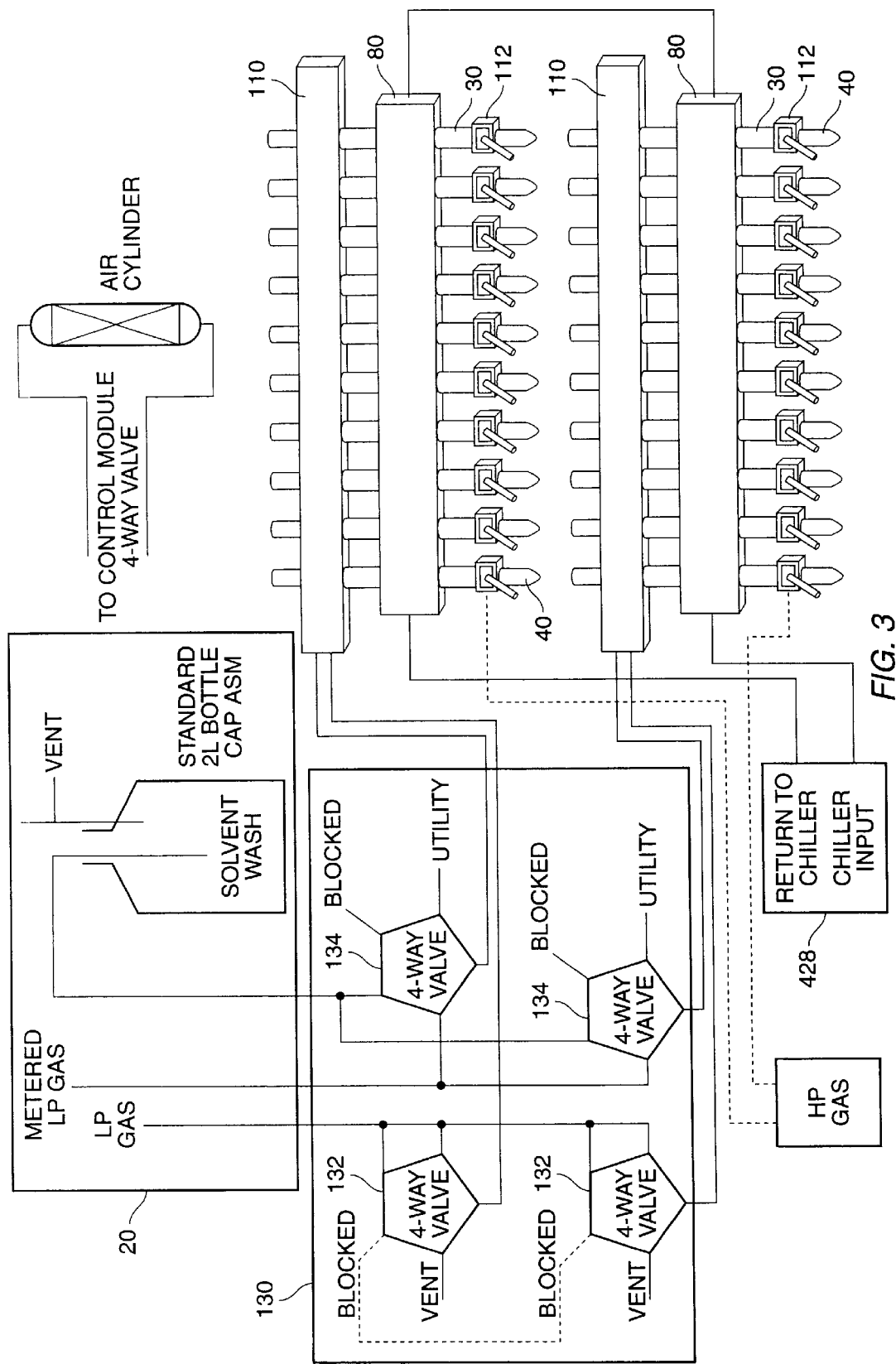
FIG. 3 is a diagram of the fluid connections for the apparatus in FIG. 2.

As can be seen in FIG. 2, two sets of reaction vessels 30 (10 per set), common manifolds 110, heat exchangers 80, and valve manifolds 114, can be found on the support structure 100, one set on each side of the structure. As can be seen in FIG. 3, each set of reaction vessels 30 and their corresponding common manifold 110 preferably have connections to liquid and gas sources 20 separate from one another. In this embodiment, each common manifold 110 has its own set of valves 132 and 134 located in upper housing 130 which can control the flow of fluid from the liquid and gas sources 20. Advantageously, having separate connections to the liquid and gas sources 20 allow the apparatus 10 to run the same or different synthesis processes in the two sets of reaction vessels. Having separate sets of connections to the liquid and gas sources 20 allows the operator to vary the liquid and the timing of liquid releases into the reaction vessels.

A. Common Manifold

Figure 4:
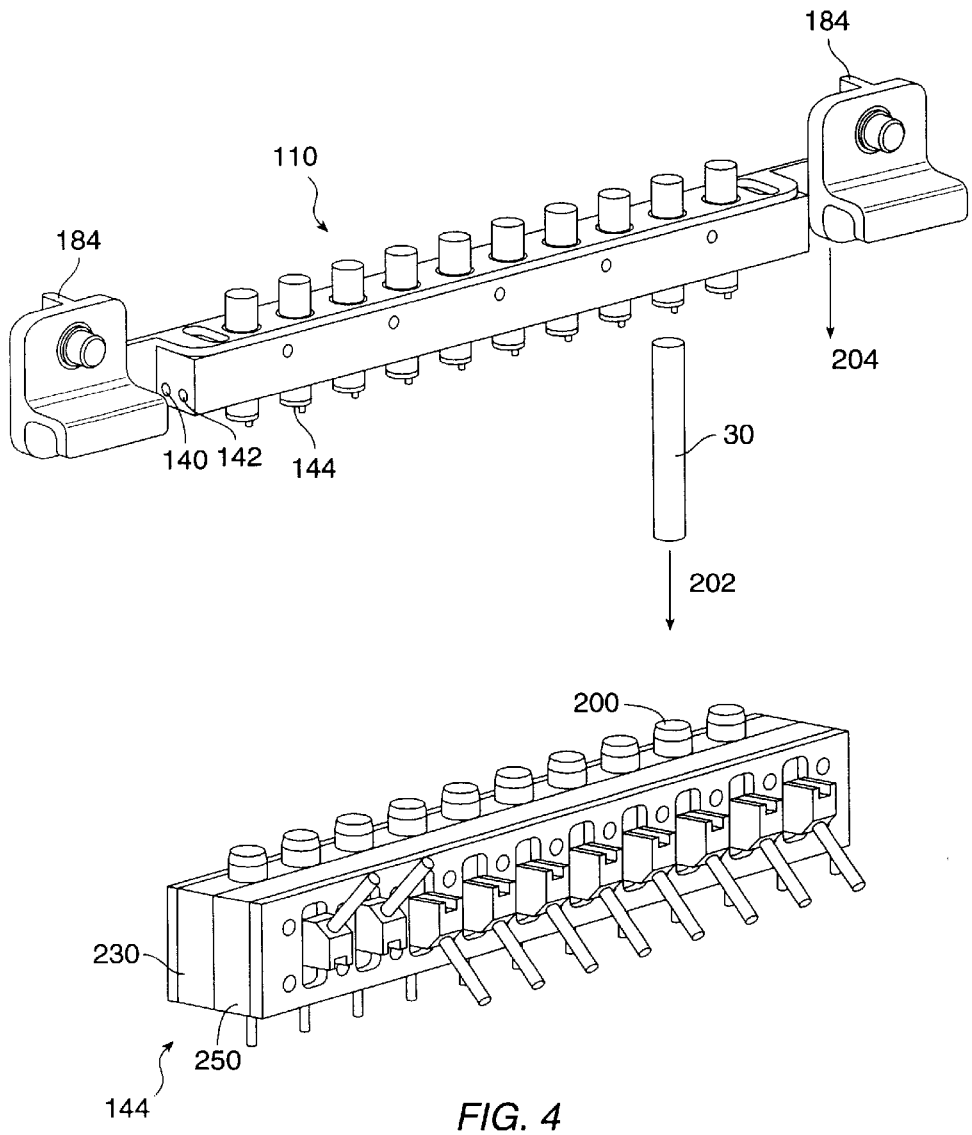
FIG. 4 is an exploded view showing a common manifold, a reaction vessel, and a valve manifold of the apparatus in FIG. 2.

Referring now to FIG. 4, a preferred embodiment of common manifold 110 will now be described. The common manifold 110 typically contains common liquid line 50 and common gas line 60 which supply liquid and gas to the plurality of reaction vessels 30 coupled to the common manifold 110. Ports 140 and 142 on the manifold 110 provide access to common liquid line 50 and common gas line 60. Although common liquid line 50 and common gas line 60 are preferably integrated into the common manifold 110 to provide certain design and manufacturing benefits, it should be understood that the common lines 50 and 60 may be separate stand alone tubing or conduits which are not integrated into a manifold so long as the common lines remain fluidly coupled to the plurality of reaction vessels 30 during synthesis.

Figure 5:
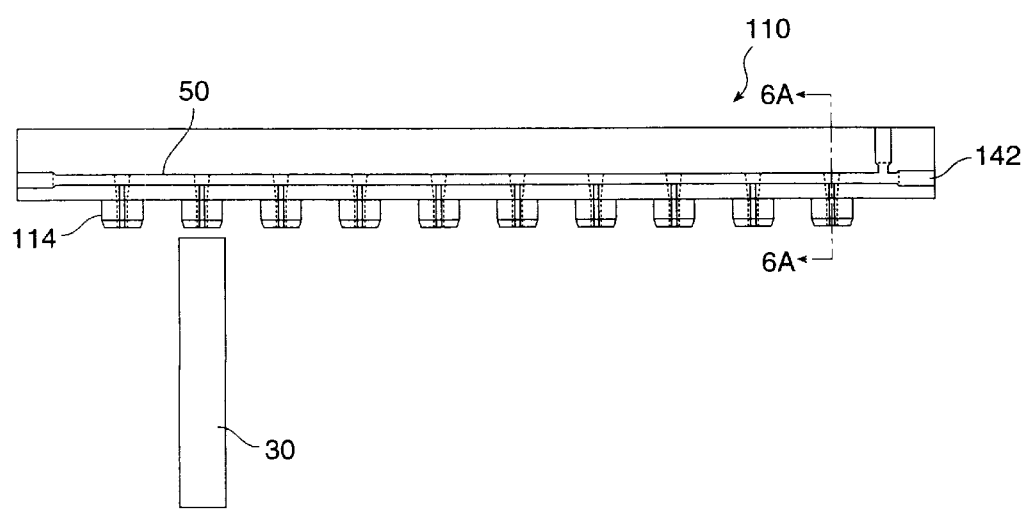
FIG. 5 shows a cross-sectional view of the common manifold of the apparatus in FIG. 2.

FIG. 5 is a cross-sectional view of a common manifold 110 showing the common gas line 60 which spans the longitudinal length of the common manifold 110. The common liquid line 50 has a substantially similar configuration within the manifold 110. The common manifold 100 has a plurality of bosses 144 that span along the longitudinal length of the manifold. In a preferred embodiment, bosses 144 are cylindrical structures having a tapered end 145, a liquid outlet port 146, and a gas outlet port 148. The boss 144 is designed to engage the inner surface of a reaction vessel 30 so as to provide an air tight seal between the reaction vessel and the common manifold 110. The outer diameter of the boss 144 is preferably larger than the inner diameter of the reaction vessel 30 so that the boss 144 interferes with the reaction vessel 30 when the two components are engaged. Engagement with the boss 144 typically causes the diameter of the reaction vessel 30 to flare and widen to accommodate the larger boss and ensure an air tight seal.

Liquid outlet port 146 and gas outlet port 148 are fluidly coupled to the common liquid line 50 and the common gas line 60, respectively. The outlet ports 146 and 148 are typically located near end 145 so as to feed into the reaction vessel 30 when the boss is engaged to the boss 144. As can be seen in FIG. 5, the manifold 110 has a plurality of bosses 144, one boss for each reaction vessel 30 coupled to the manifold. The outlet ports 146 and 148 may be constantly coupled to the reaction vessel 30 during processing. This reduces the process time needed to fluidly couple the reaction vessels to the liquid or gas sources. Further, larger diameter ports and higher flow rates may be achieved as there are fewer size restrictions on the ports. In one embodiment, the ports 146 and 148 may range in size from about 0.120 to 0.130 inches in diameter. The size may be adjusted so long as they do not interfere with access from other ports (i.e. from passage 150) into the reaction vessel 30. In the past, reaction vessels that were not constantly connected to their sources and used septums that required small diameter needles to prevent coring of the septums with each penetration.

The common manifold 110 and boss 144 preferably comprise an inert material such as, but not limited to, Teflon®, glass, propylene, polyethylene, ceramic, or stainless steel coated with Teflon®. The material used in the common manifold 110 should be able to withstand the temperature, pressure, and chemical environment to which the manifold is exposed. In general, it is preferred that all liquid wetted parts of the apparatus 10 including the common gas line 60 are formed from or covered with a chemically inert material such as Teflon®.

Figure 6A:
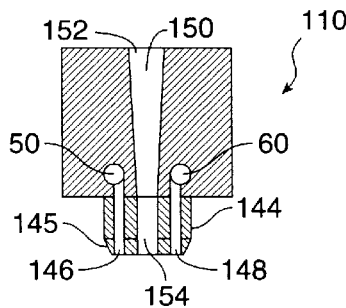
FIG. 6A depicts a cross-sectional view of the common manifold in FIG. 5 taken along lines 6A—6A.
Figure 6B:
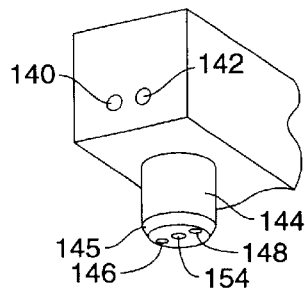
FIG. 6b is a partial perspective view of the common manifold in FIG. 5.

Referring to FIG. 6A, an exemplary embodiment of the common manifold 110 incorporates an access passage 150 that has an access inlet 152 and an access outlet 154. The access passage 150 facilitates the introduction of reagents into the reaction vessel 30 during processing. Access inlet 152 is typically located on an upper surface of the manifold 110, while access inlet 154 is typically located on end 145 of boss 144 so as to feed into the reaction vessel 30. The passage 150 preferably has a tapered configuration where the cross-sectional area of the passage 150 is greater near the inlet 152 then at outlet 154. The access inlet 152 is typically a circular opening having a diameter between about 0.170 and 0.250 inches, preferably between about 0.175 and 0.185 inches. The inlet 152 is sized to facilitate the introduction of a pipet or other instruments used to deliver liquid or powdered solid reagents into the reaction vessel 30.

Figure 7B:
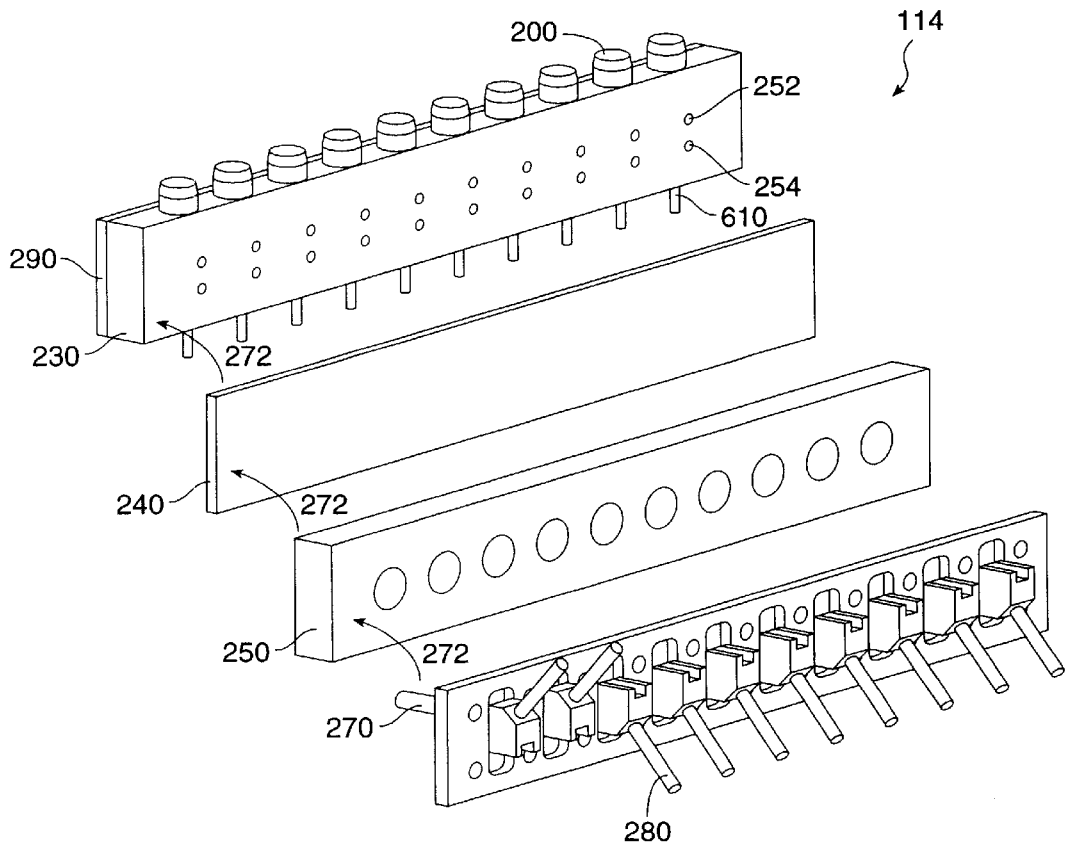
FIG. 7B is an exploded view of the components of a preferred embodiment of the valve manifold.
Figure 7A:
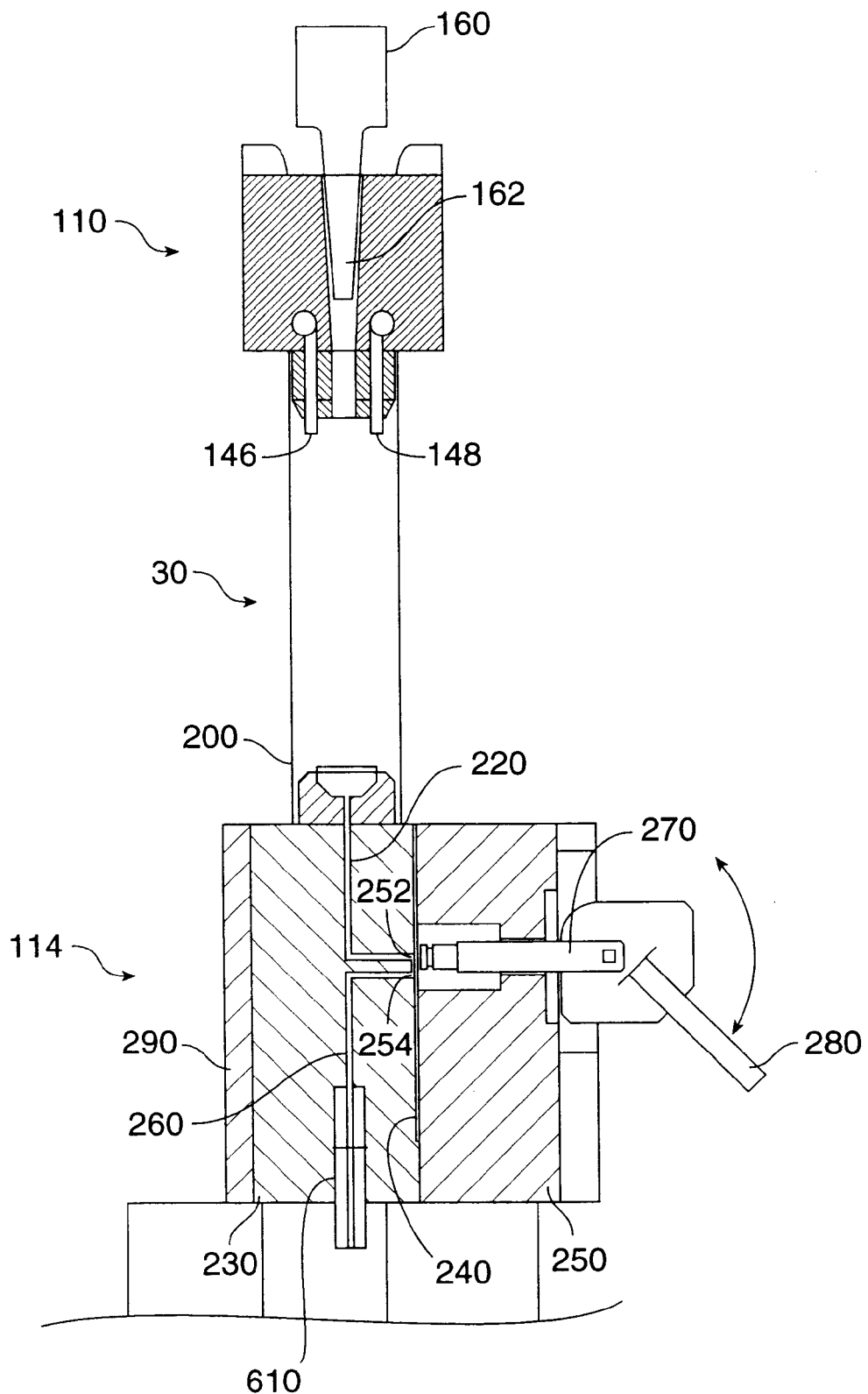
FIG. 7A shows a vertical sectional view of the common manifold, the reaction vessel, and the valve manifold according to a preferred embodiment of the present invention.

As shown in FIG. 7A, the passage 150 typically has a sealing device 160 such as a plug having a distal tip 162 conformed to fit the contour of the passage 150. It should be noted that other sealing devices such as a cap or an articulating flap may be used so long as they can suitably cover and uncover the passage 150. The sealing device 160 may be made from a variety of materials such as Tefzel® which can conform to the passage 150 and provide an air tight seal. The sealing device 160 can withstand pressures up to 60 psi, preferably up to 70 or more psi. In a preferred embodiment, the distal tip 162 is made from or coated by an inert material which will not contaminate the chemical synthesis. During the addition of reagent, the sealing device 160 is removed from the passage 150, and inert purging gas such as argon or nitrogen is introduced into the reaction vessel through gas outlet port 148. The positive pressure created by the flow of inert gas into the reaction vessel 30, prevents air from entering into the reaction vessel while the sealing device 160 is removed. In this manner, special reagents can be added to the reaction vessel during chemical synthesis while substantially minimizing the risk of contaminating the environment in the reaction vessel 30.

Advantageously, the common liquid line 50 and the common manifold 110 facilitates common washing of each of the reaction vessels 30 simultaneously, which significantly reduces the physical burden on the operator. Referring to FIGS. 3 and 5, a common liquid line 50 can be used to feed a common wash fluid from a liquid source 20 to flood fill the ten reaction vessels 30 coupled to the boss 144 on the common manifold 110. Alternatively, the common liquid line 50 may be used to add solutions of a reagent to each of the reaction vessels 30 simultaneously. Further, the liquid line 50 is typically constantly coupled to the reaction vessel 30 during synthesis. This constant connection reduces the time required to introduce liquids into the reaction vessel 30 and also maintains a closed environment that reduces the risk of contamination.

The common gas line 60 also facilitates the synthesis of combinatorial chemical libraries by allowing the introduction of either direct low pressure gas or metered low pressure gas through gas outlet port 148 into the plurality of reaction vessels 130. A metered low pressure gas in the range of about 8 to 12 psi is introduced into the reaction vessels to prevent contamination when additional reagents are being added through access passage 150. A direct low pressure gas typically in the range of 8 to 12 psi is used to facilitate the flushing and draining of liquid from the reaction vessel 30 as may be required during the various process steps of chemical synthesis, as described below. The gas introduced into the reaction vessel environment is preferably a chemically inert gas such as argon or nitrogen. The introduction of these gases into the plurality of reaction vessels 30 facilitates draining and purging procedures.

Referring to FIGS. 2 and 4, the common manifold 110 and collector 116 are preferably slidably mounted on rails 170 and 172 formed in the support structure 100, respectively. The valve manifold 114 and heat exchanger 80 are typically fixedly secured to the support structure 100 since these components of apparatus 10 are typically the heavier and more technically involved components of the apparatus. Hence, it would be desirable that they remain in the fixed position on the support structure 100. As noted by arrow 171, the rails 170 allow the common manifold 110 to slide between a first position where the manifold engages the reaction vessels 30 and a second position where the manifold is moved away from the reaction vessels. The upper manifold 110 has a handle 180 acts as a sliding device as it is guided along the rails 170. The handle 180 also has a button 182 which can be pushed to release a locking device 184 that mates with circular cut-outs 186 and the rail 170. The cut-outs 186 may be located at both the first and second positions. A variety of other device known in the art may be used to provide movement of the common manifold 110 and the connector 116 along the support structure 100.

Figure 8A:
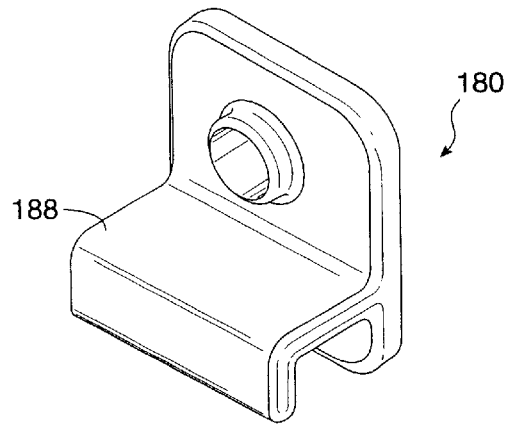
FIGS. 8A and 8B show a preferred embodiment of a sliding device according to the present invention.
Figure 8B:
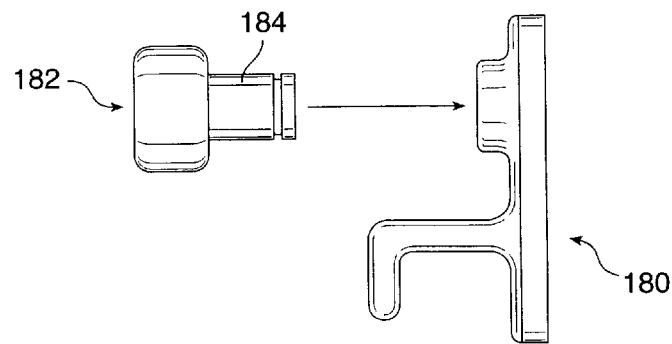

The handle 180, as shown in FIGS. 8A and 8B, has a grip or pressure surface 188 that allows a user to raise or lower the handle and the manifold 110 along the rail 170. The grip 188 allows the operator to exert force on the upper manifold 110 to compress the upper manifold 110 and its bosses 144 onto the reaction vessels 30 to ensure an air tight seal between the components. The force also compresses the reaction vessels 30 onto the valve manifold bosses 200 (FIG. 4). The handle 190 attached to the collector 166 and traveling along rail 172, is substantially similar in design to the handle 180. It should be understood that other locking and sliding mechanisms known in the art may be used with handles 180 and 190 to facilitate the motion of these two components of apparatus 10.

B. Valve Manifold

Referring now to FIG. 4, a preferred embodiment of the valve manifold will now be described. As discussed earlier, the valve manifold 114 is typically fixedly secured to the support structure 100 as shown in FIG. 2. At the start of the synthesis process, new reaction vessels 30 as shown in FIG. 4 are placed through the heat exchanger 80 (see FIG. 12) and placed onto valve boss 200 shown by arrow 202. With reaction vessels 30 positioned over a plurality of valve bosses 200, the common manifold 110 is then lowered onto the reaction vessels 30 as shown by arrow 204. The common manifold bosses 144 engage the first opening on the reaction vessels 30. The common manifold 110 is forced downward onto the reaction vessels 30 until the first and second openings of the reaction vessel 30 flair and engage bosses 144 and 200, respectively, to form an air tight seal between the reaction vessel 30 and the bosses.

FIG. 7A shows a vertical cross-section of the resulting synthesis environment when the common manifold 110 and the valve 114 are coupled to a reaction vessel 30. Reagents are added to the reaction vessel 30 through common manifold 110. Referring to FIG. 3, when liquid is added to the reaction vessel 30, the valve 132 is typically placed in the venting position so that inert gas in the reaction vessel 30 that is displaced by the introduction of liquid through port 146 may exit through port 148 and out through the vent coupled to valve 132. When it is desired to flush liquid from the reaction vessel 30, valve 134 in FIG. 3 is coupled to a direct low pressure gas source which then introduces preferably inert low pressure gas into the reaction vessel 30 through port 148. This expedites the passage of liquid over the frit 32 (FIG. 1B) and into exhaust passage 220.

In this preferred embodiment of the valve manifold 114, the exhaust passage 220 is formed in the valve manifold boss 200 and valve manifold core 230. To ensure that chemicals exiting the exhaust passageway 220 do not contaminate the reaction vessel or cause corrosion in the exhaust passage 220, the valve manifold core is typically made entirely from an inert material such as Teflon® with the exhaust passageway drilled or otherwise formed in the core 230. A thin membrane 240 typically made of Teflon® is sandwiched between the core 230 and the valve pin guide 250. The membrane 240 has a thickness between about 0.008 to 0.12 inches, preferably between about 0.009 to 0.011 inches. The membrane 240 acts as a flow control member, covering the outlet 252 of exhaust passage 220 and the inlet 254 to the lower exhaust passage 260. When pin 270 is retracted by the rotation of lever 280, as shown by arrow 282, the pin 270 is retracted away from the outlet 252. This retraction allows fluid to flow from outlet 252 to inlet 254. The assembly of a preferred embodiment of the valve manifold 114 is shown in FIG. 7B where the components of the manifold are typically screwed or otherwise joined together. Arrows 272 show how the various components are connected. Details on this and other suitable valves may be found in co-pending U.S. patent application Ser. No. 08/560,728, filed Nov. 20, 1995, the full disclosure of which is incorporated herein by reference.

Figure 9:
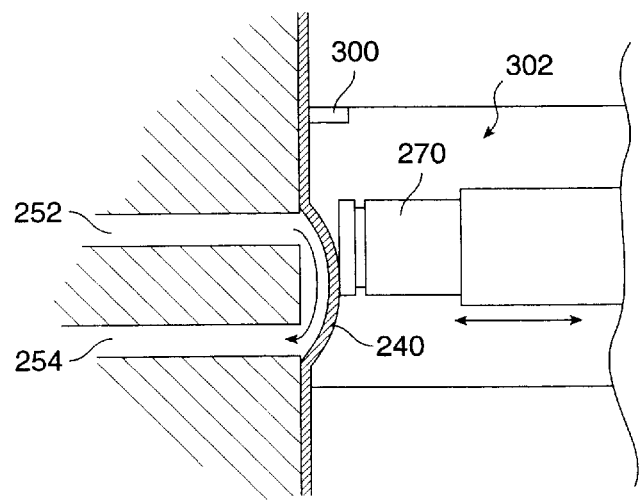
FIG. 9 shows a partial cross-sectional view of a valve according to the present invention.

As shown more clearly in FIG. 9 the retraction of pin 270 allows the membrane 240 to be deflected by the pressure from liquid and high pressure gas exiting outlet 252. The deflection that occurs may be very small, in the range of about 0.02 to 0.03 inches, since liquid flow is typically pressed out by high pressure gas in the reaction vessel 30. The membrane 242 guides the mixture of liquid and high pressure gas into inlet 254 of lower exhaust passage 260 which directs the material to the collection vessels. The valve manifold has a reinforcement plate 290 made of material such as aluminum or stainless steel to provide structural support to the valve manifold core 230 which is typically made of a flexible material such as Teflon®. The pin guide 250 which is not in direct contact with material leaving the reaction vessels 30 is made of materials such as aluminum or stainless steel.

Figure 10:
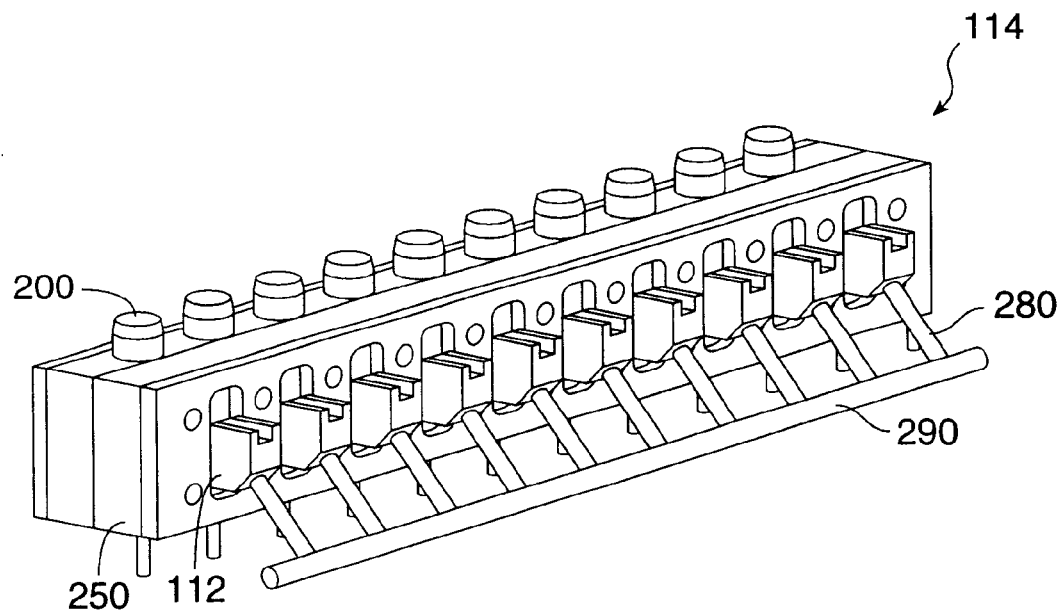
FIG. 10 is a perspective view of one embodiment of the valve manifold of the present invention.
Figure 11:
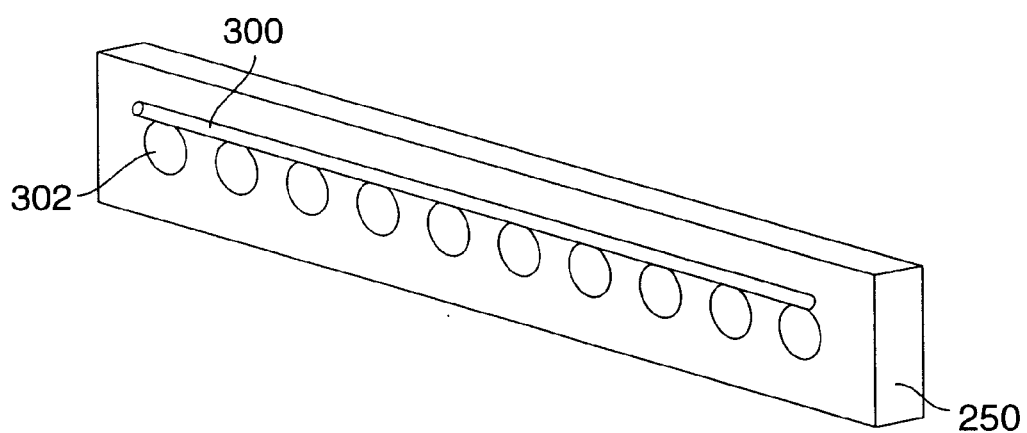
FIG. 11 is a perspective view of the pin guide plate according to the present invention.

Referring to FIGS. 3 and 10, the draining of liquid from the reaction vessels 30 requires the opening of valves 112 which are typically mounted in a valve manifold 116, and the introduction of high pressure gas into the reaction vessel 30. As can be seen in FIG. 3, each reaction vessel 30 has its own valve 112 and the draining of a large number of reaction vessels requires the manual switching of the valves 112 associated with the many reaction vessels 30. To facilitate the simultaneous draining of a bank of reaction vessels 30, FIG. 10 shows the levers 280 of each valve 112 coupled to a crossbar 290 that allows an operator to simultaneously open or close all valves located in the valve manifold 116. It should be understood that the number of valves activated by the crossbar 290 can be varied by changing the number of levers connected to the crossbar or varying the length of the crossbar 290.

In a preferred embodiment, the valve pin guide plate 250 has a channel 300 for conducting a gas into the chambers 302. This channel 300 provides for the automated opening and closure of all the valves connected to the channel. With pin 270 pushed away from the membrane 240, pressurizing chamber 302 causes the membrane 240 to be pushed against the ports 252 and 254 sealing the reaction vessel from the collector 116. The gas applied to the channel 300 is typically a higher pressure gas source than the one which introduces gas into reaction vessels 30 during draining. As shown in FIG. 3, a high pressure gas source 272 typically having a pressure between about 30 to 45 psi may be connected to the valves. As shown in FIG. 9, the pressure from this gas would create a sealing force on the membrane 240 without using the mechanical pin 270. When this gas source is removed, the plurality of valves 112 in the manifold 114 are open and draining the reaction vessels 30. This allows automated simultaneous draining of the reaction vessels 30. The pneumatic actuation of the valves 112 is typically regulated by the controller 70.

C. Heat Exchanger

Figure 12:
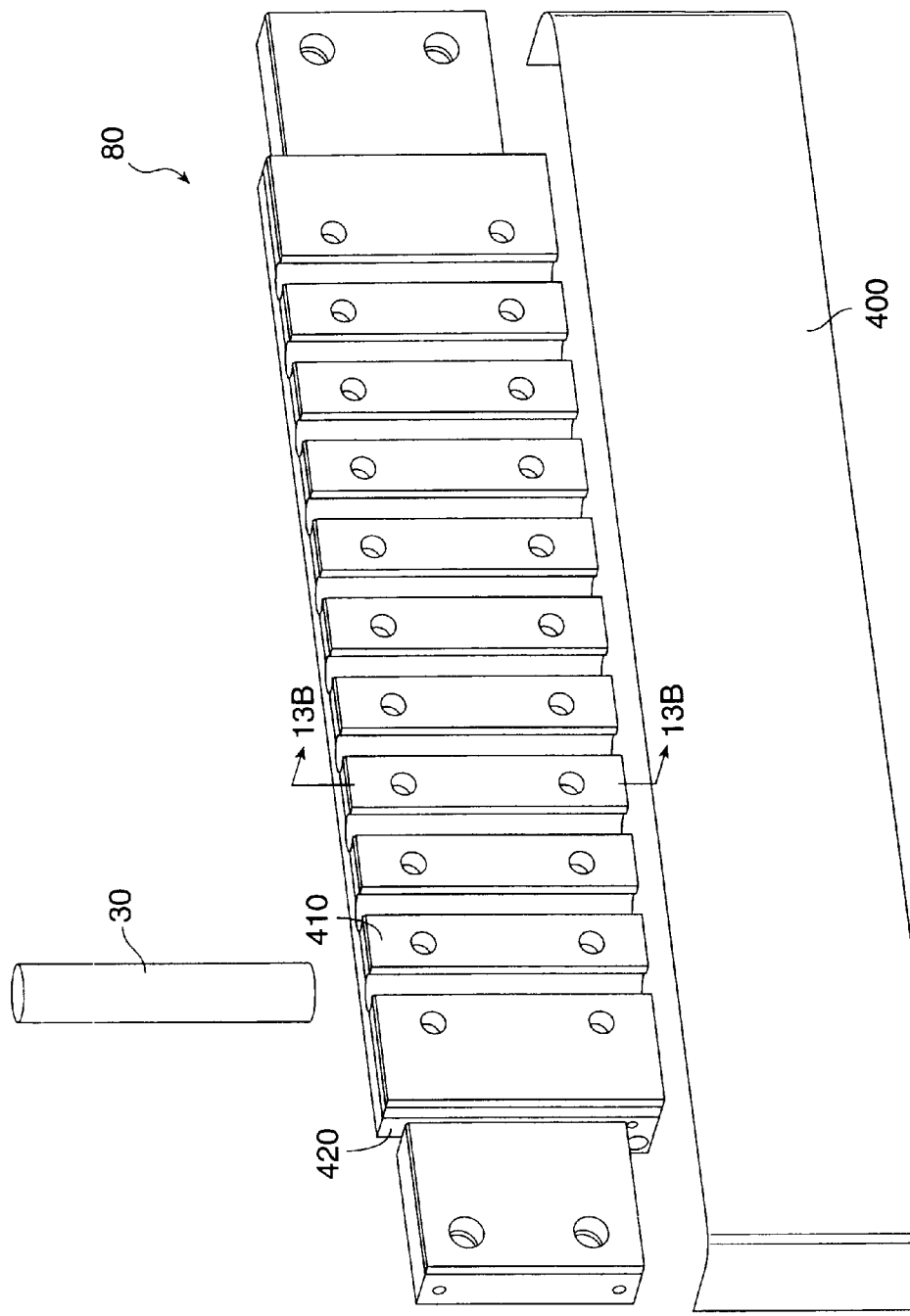
FIG. 12 is an exploded view of the heat exchanger according to the present invention.
Figure 13A:
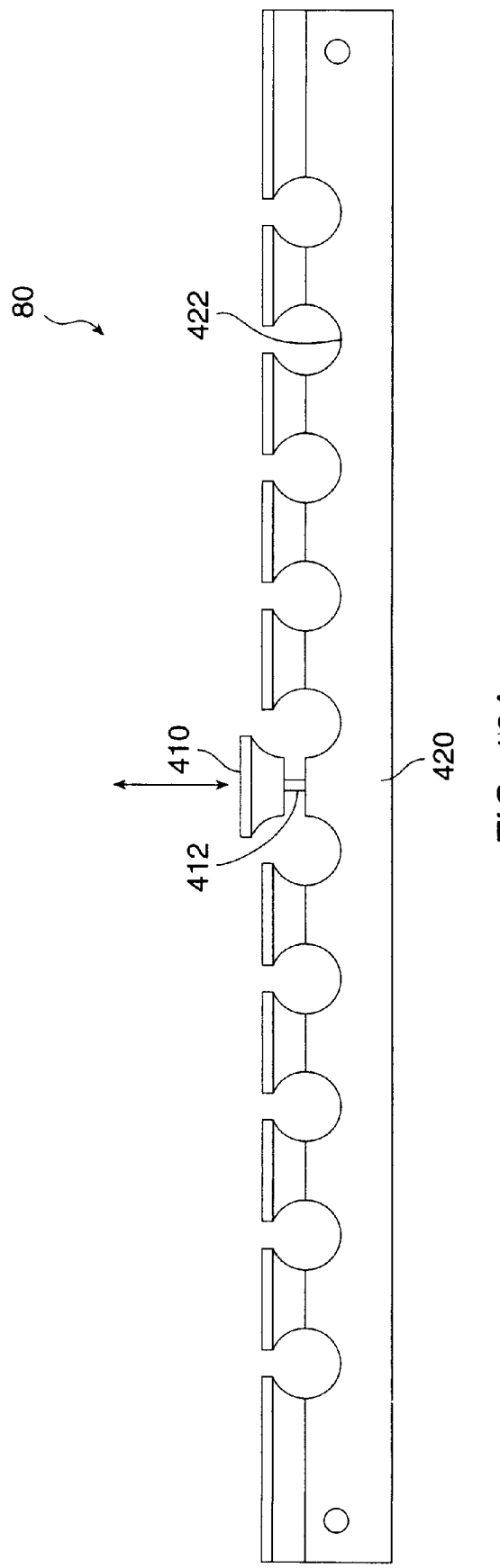
FIG. 13A is an elevated view of the heat exchanger in FIG. 12.

Referring now to FIGS. 2 and 12, a preferred embodiment of the heat exchanger 80 will now be described. As shown in FIG. 2, the heat exchanger 80 is typically covered by an outer thermal shield 400 which prevents accidental contact between the operator and the heat exchanger 80 during chemical synthesis. The outer shield 400 (FIG. 12), which is typically made of polycarbonate or glass, is designed such that reaction vessels 30 may be inserted or removed from the valve manifold 114 with the heat shield in place (i.e. attached to heating block 420). Removal or insertion of the reaction vessels 30 occurs when the common manifold is raised away heat exchanger 80. A plurality of fittings 410, having an inner surface that conform to the contours of the reaction vessels 30, are used to hold the reaction vessels 30 to the heat exchanger 80. The fittings 410, as shown in FIG. 13A, may be mounted on a pair of spring loaded shoulder screws 412 that allow the fitting 410 to be pulled away from the thermal block 420. Thermal block 420 has a plurality of curved grooves 422 which conform to the contour of reaction vessel 30. The fittings 410 are pulled away from the thermal block 420 to allow the reaction vessel 30 to be inserted into the heat exchanger 80. Once the reaction vessel is in place the fitting 410 is released to press against the outer surface of the reaction vessel 30. This ensures that their is good thermal contact between reaction vessels 30 and the thermal block 420.

Figure 13B:
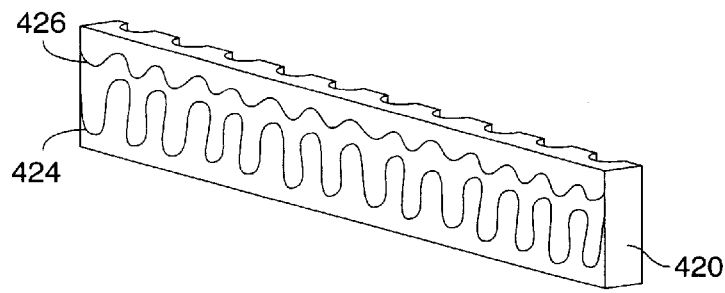
FIG. 13B depicts one embodiment of the chiller and heating coil used in a heat exchanger according to the present invention.

In a preferred embodiment of the thermal block 420, a heating element 424, a cooling channel 426, are both embedded in the thermal block 420 (FIG. 13B). The thermal block 420 should be able to provide heating and cooling in the range of about −40° C. to 150° C., preferably about −50° C. to 200° C. It should be understood, however, that the heating element 424 and the cooling channel 426 may be housed in separate thermal blocks. In an exemplary embodiment of the apparatus 10, the thermal block 420 contains a heating element that assumes a serpentine configuration in the thermal block 420. The heating element would be able to deliver a substantially even distribution of thermal energy to the reaction vessels 30 such that temperature variance at any point on the thermal block 420 will be in a range of about ±4°, preferably ±2° C. The heating element 424 may be made from a variety of materials such as Kapton, which allows for adjustment of power density in the heating element and is generally chemically resistant. The spacing between the serpentine or otherwise configured heating element 424 may be adjusted to vary thermal distribution or area of heating from the thermal block 420. The cooling channel 426 is typically a fluid flow channel that passes a coolant, such as water and an additive such as "antifreeze," through the thermal block 420 at temperatures between about −20° to −50° C., preferably between about −35° to −45° C. The coolant is pumped into the channel 426 through a chiller 428 (FIG. 3).

D. Agitator Assembly

As discussed earlier, agitator 35 such as a Teflon® covered magnet is located within the reaction vessels 30. These agitators 35 are moved longitudinally along the inner surface of the reaction vessels 30 to generate liquid circulation within the reaction vessels. The agitators 35 are moved by the force of a magnet 500 positioned externally to the reaction chamber 30. Typically an array of magnets 500 are used to move the agitators 35 in the plurality of reaction vessels 30. The magnets 500 are preferably mounted on a common actuator arm 502 to provide for uniform movement and mixing with the reaction media in the reaction vessel 30. The magnet 500, arm 502, and mechanical actuator 504 comprise an agitator assembly 506.

Typically, an array of magnets 500, one for each reaction vessel 30, is moved back and forth via a mechanical coupling to the actuator 504, such as an air cylinder drive or an electrical drive. The push/pull air cylinder is controlled by an electronic circuit via a solenoid valve. The distance the agitators 35 move inside the reaction vessel 30 may be controlled by mechanical stops on the actuator 504. The rate at which the agitators move back and forth is controlled by an electronic circuit or controller 70 which may set an appropriate mixing stroke, for example, from 1 to 10 seconds/stroke. In the present embodiment, the actuator arm 502 containing the array of magnets 500 is typically moved by an actuator 504 such as a pneumatic piston which is vertically coupled to the actuator arm 502. The piston moves in a reciprocal motion as shown by arrow 508 to stimulate liquid or reaction media circulation in the reaction vessels 30.

Figure 14:
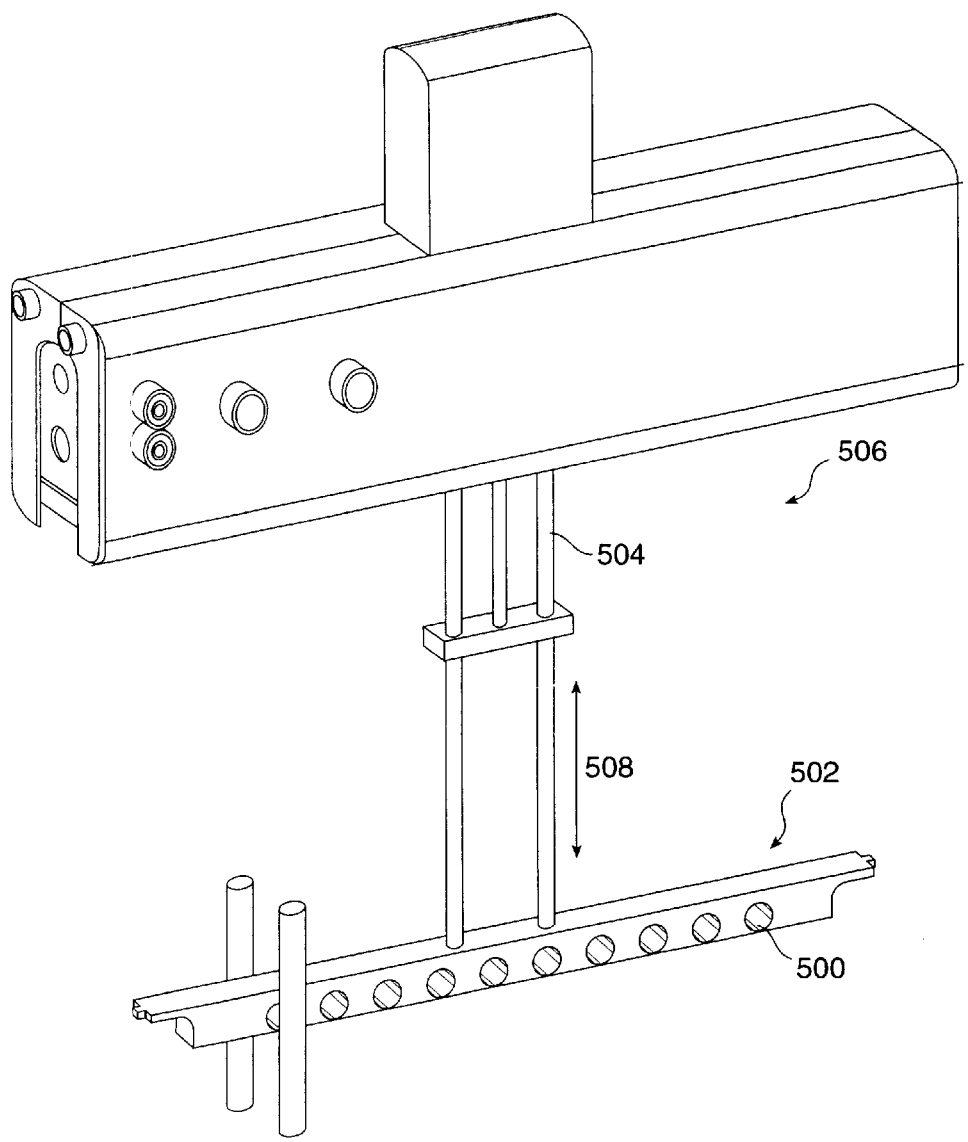
FIG. 14 is a perspective view of an actuator arm and magnet array according to one embodiment of the present invention.

As shown in FIG. 14, in a preferred embodiment of the actuator arm 502, the arm is located between the two sets of reaction vessels which are secured on each side of the support structure 100. Positioning the actuating arm 502 and the magnets 500 between the sets of reaction vessels 30, reduces the amount of material used to form the actuator arm and thus provides certain manufacturing and cost efficiencies.

The magnets used in the actuator arm 502 are preferably neodymium or neodymium-iron-boron magnets which provide high levels of magnetic attraction and resistance to thermal shock. It should be understood, however, that other magnetic devices may be used so long as they provide the desired magnetic strength over the range of operating temperatures.

E. Collector

Referring now to FIGS. 2, 7, and 15, a preferred embodiment of a collector 116 and the collection vessels 40 will now be described. As shown in FIG. 15, the collector 116 typically comprises a housing 602 which contains a plurality of collection vessels 40 which receive drainage fluid exiting the reaction vessel 30 through lower exhaust passage 260 (FIG. 7). The lower exhaust passage 260 typically has a nipple or other extension 610 (FIG. 7) that directs liquid exiting the exhaust passageway into the collection vessels 40. Although the present embodiment has one collection vessel 40 for every reaction vessel 30, it should be understood that a variety of different types and numbers of collection vessels can be used for containing liquid exiting from the reaction vessels 30. The present embodiment of the collector 116 also has handle 604 similar to the handle 180 on the common manifold 110 so as to allow the collector 116 to be slidably adjusted to or away from the valve manifold 114.

F. Controller and Multiple Liquid Sources

Figure 16:
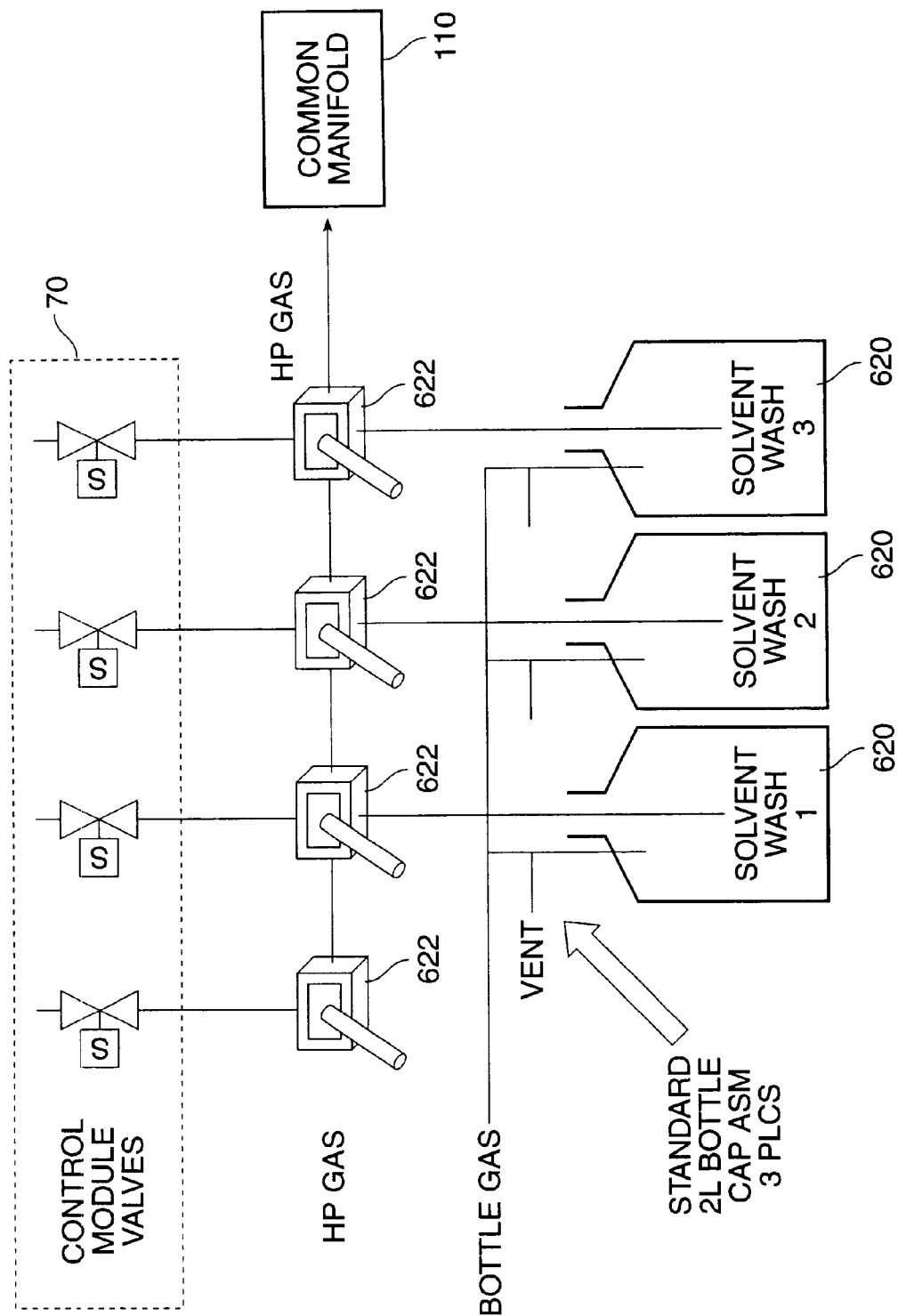
FIG. 16 is a schematic diagram of one embodiment of a controller according to the present invention.

FIG. 16 shows a controller 70 which regulates a plurality of liquid sources 620. The controller 70 operates a plurality of valves 622 which controls the liquid flow from the liquid sources 620. This allows the controller 70 to introduce a variety of different liquids in a successive manner into the common manifold 110 which leads to the reaction vessels 30. This embodiment of the controller 70 provides a greater level of automation since the operator does not need to manually switch the connections to the various liquid sources 620 to perform these synthesis procedures.

III. Alternative Embodiment of the Apparatus

Figure 17:
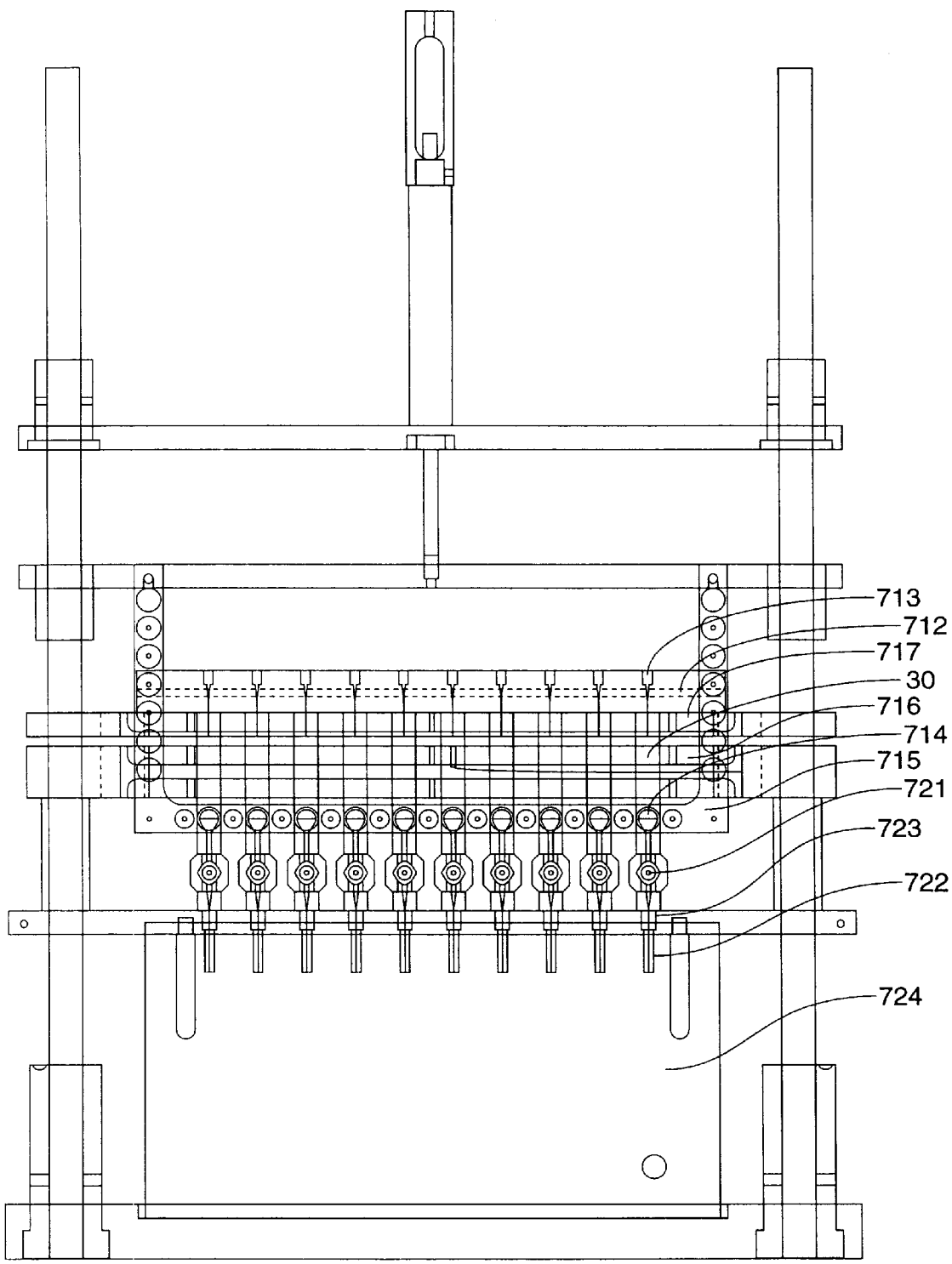
FIG. 17 is a vertical sectional view of an alternative embodiment of the apparatus of the present invention.

FIG. 17 is a diagrammatic cross-sectional side view of the chemical synthesizer as may be used in an alternative embodiment. This cross-sectional view depicts one side of the chemical synthesizer apparatus. This specific chemical synthesizer apparatus employs a total of 20 reaction vessels 30 which are oriented in two rows of 10 reaction vessels 30. Each reaction vessel 30 is mounted in the chemical synthesizer by clamping into the heat exchanger 716.

A common manifold 712 contacts the upper opening of each reaction vessel 30. The common manifold 712 bears a gas inlet port (not shown) and a fluid inlet port (not shown) and an access port 713 above each reaction vessel to facilitate the introduction of reagents. A magnetic or ferrous agitator 35 moves longitudinally back and forth along the inner surface of each reaction vessel 30 under the force of a magnet 714 positioned externally to the reaction vessel. Each magnet 714 is mounted on a common actuator arm 715 to provide for uniform movement and mixing of the reaction media. A heat exchanger 716 contacts the outer surface of each reaction vessel on the lower portion of the reaction vessel and a cooling block 717 contacts the outer surface of each reaction vessel on the top portion of the reaction vessel. Each reaction vessel bears a valve 721 attached to the lower outlet of the reaction vessel. The outlet port of each valve 721 bears a nipple 722 which is inserted into a common vacuum system 724 to facilitate washing, draining and removal of product which has been cleaved from its optional support.

A. Heat Exchanger

Figure 18:
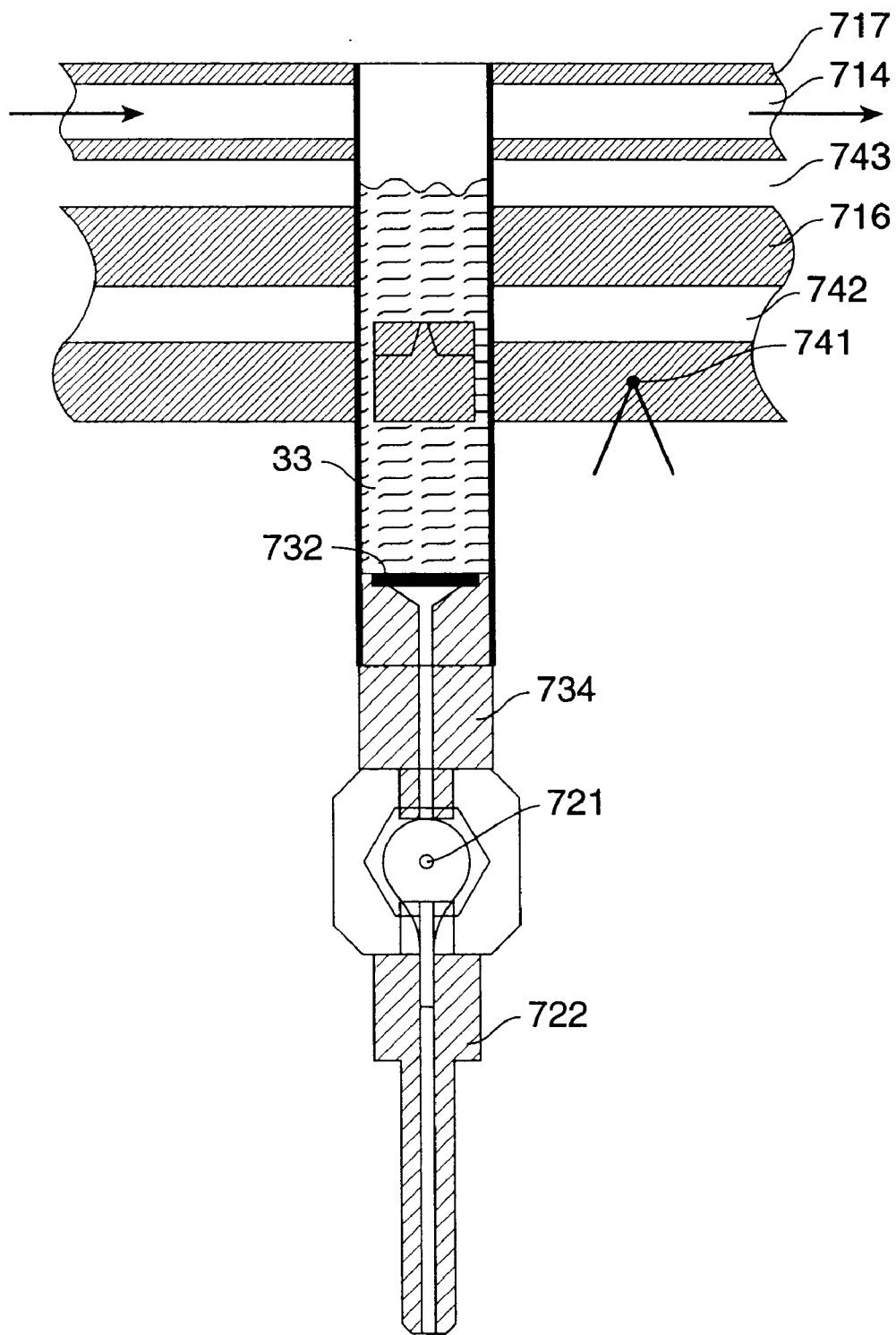
FIG. 18 shows a partial sectional view of a reaction vessel, heat exchanger, and valve of the apparatus in FIG. 17.

Referring now to FIG. 18, a diagrammatic cross-sectional side view of the reaction vessel 30 of FIG. 1B is shown including a heat exchanger 716 which contacts the outer surface of each reaction vessel on the lower portion of the reaction vessel and also including a cooling block 717 which contacts the outer surface of each reaction vessel on the top portion of the reaction vessel.

In a preferred embodiment the heat exchanger 716 is comprised of a metal heat exchanger, such as an aluminum, copper or steel heat exchanger. The heat exchanger may also be constructed of other materials which conduct heat and which may be milled to the appropriate specifications. Two arrays of 10 reaction vessels fit into the two part metal heat exchanger. A front cover part (not shown) secures the reaction vessels in place and provides about a 360 degree wrap of metal around each vessel thereby ensuring good thermal contact with each of the reaction vessels. The front cover has observation windows to allow visual monitoring of the reaction media through the side wall of the reaction vessel.

To heat the reaction vessels, an electric heater (not shown), such as a 400 watt electric rod heater, which is embedded in or affixed to the heat exchanger is activated. Alternate methods for heating the heat exchanger such as hot water, hot air, or steam are also envisioned. A thermocouple 741 (graphically depicted) which is embedded in or affixed to the aluminum heat exchanger is used to sense the temperature of the heat exchanger. A process temperature controller (not shown) applies current to the electric heater and controls the temperature of the heat exchanger based on the thermocouple measurement via an internal feedback mechanism. The heat exchanger also bears a tube 742, such as a copper or aluminum tube, passing through it. Similarly, cooled liquid, gas or refrigerant can be passed through the copper tube to chill the aluminum heat exchanger and reaction columns thereby providing for reactions at below ambient temperature.

To reduce solvent evaporation, it is preferred that a cooling block 717 contact the outer surface of each reaction vessel on the top portion of the reaction vessel. This cooling block 717 is preferably comprised of a metal such as aluminum or copper and is mounted above the heat exchanger 716 with an insulating space 743, such as an air gap or suitable insulating material, in between. The cooling block 17 bears a tube 744, such as a copper or aluminum tube, in which chilled liquid or gas (such as cold water, brine, alcohol chilled with dry ice, liquid nitrogen, refrigerant, and the like) can be passed through thereby cooling the top portion of each reaction vessel 30. Therefore the lower heat exchanger 716 can heat the liquid in the reaction vessel 30 while the upper cooling block 717 can cool and re-condense evaporated fluid vapors. By heating the bottom portion of a reaction vessel and cooling the top portion of a reaction vessel a reflux of the solvent in the reaction mixture may be achieved. The heat exchanger 716 and the cooling block 717 also serve to clamp and seal the tops of each reaction vessel 30 to the common manifold 712.

B. Common Manifold

Figure 19:
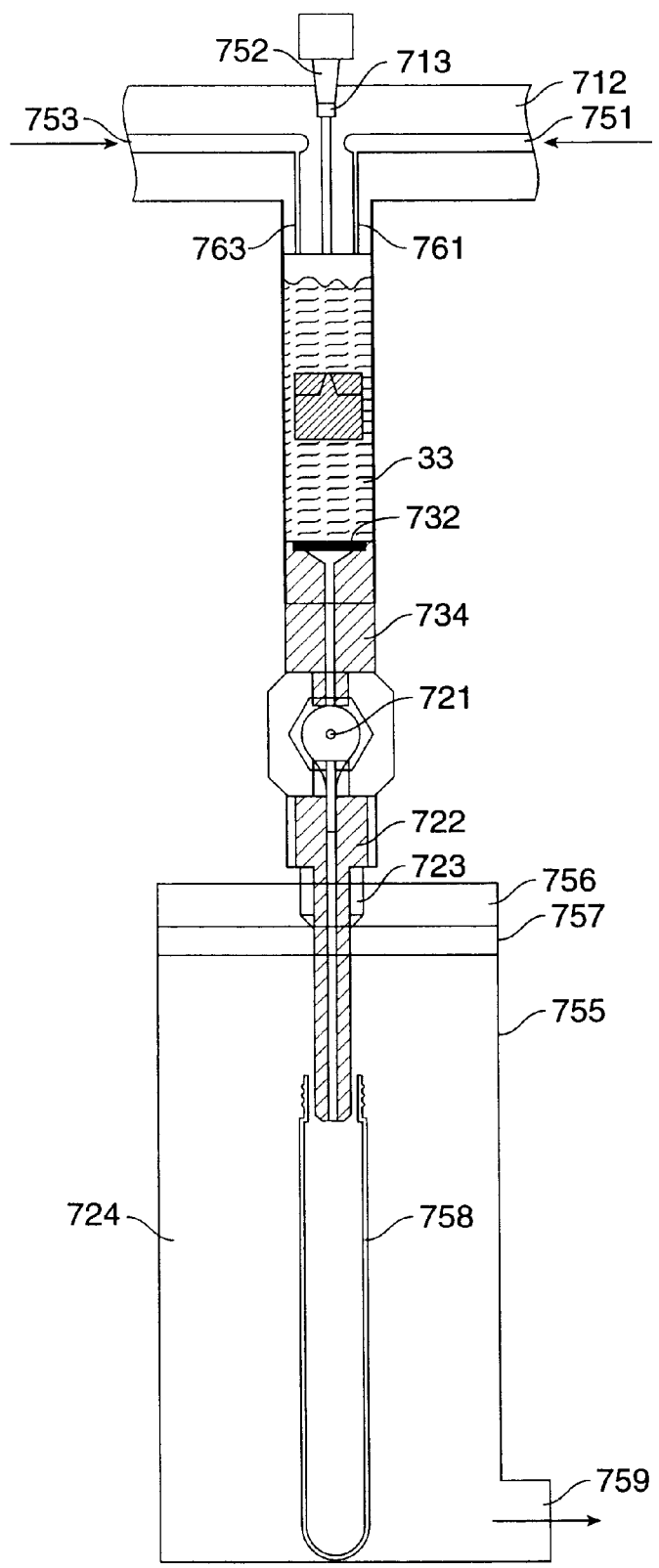
FIG. 19 shows a partial sectional view of a common manifold, reaction vessel, valve, and collection vessel of the apparatus in FIG. 17.

Referring now to FIG. 19, a diagrammatic cross-sectional side view of the reaction vessel 30 of FIG. 2 is shown including a common manifold 712 which bears a fluid inlet line 753. The fluid inlet port (not shown) connects to the fluid inlet line 753 which runs down the length of the common manifold 712. Optionally, the fluid inlet port may additionally comprise a valve. In the specific preferred embodiment, the common manifold is made from an inert material, such as a solid piece of Teflon®, which possesses a fluid inlet port which connects to a fluid inlet line 753 running linearly along the inside of the common manifold and a plurality of fluid outlets 763 roughly perpendicular to the fluid inlet line 753 wherein each fluid outlet 763 is positioned to feed into the upper opening of each reaction vessel 30. The fluid inlet line 753 in the common manifold 712 facilitates common washing of each of the reaction vessels 30 simultaneously. A common wash fluid can be fed into the common manifold (flow diagrammatically depicted by arrow) to flood fill ten columns simultaneously. Alternatively, the fluid inlet line 753 may be used to add solutions of a reagent to each of the reaction vessels 30 simultaneously.

Referring again to FIG. 19, common manifold 712 may include an access port 713 above each reaction vessel to facilitate the introduction of reagents. Special reagents can be added to each reaction vessel 30 using the access port 713 above each reaction vessel 30. Each access port 713 feeds into the top of each reaction vessel 30. Reagents can be dispensed into the reaction vessel 30 through the access port 713, for example by using a syringe needle. During the addition of reagent, inert gas can flow out the access port 713 thereby preventing air from entering into the reaction vessel 30. After reagent is added into the reaction vessel 30, the access port 713 is sealed with a plug 52, such as a stainless steel or Teflon® male Luer plug.

C. Controller

The electronics controller (not shown) comprises a process controller to control the temperature of the heat exchanger 716. The process controller permits temperature adjustment and ramp, soak, and cool down programming.

The electronics controller further comprises circuitry to control the mixing rate in the reaction vessels via the common actuator arm 715 which is coupled to the air cylinder driven mixer. The electronics controller permits the mixing rate to be adjusted easily. The electronics controller may further comprise a timing circuit to permit cycling of the inert gas feeding the reaction vessels. Teflon® coated cables run from the electronic controller to the chemical synthesizer.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, apparatus other than the particular device as set forth herein above may be applicable as a consequence of variations in the reagents or methodology to prepare compounds from the invention indicated above. Expected variations or differences in the results are contemplated in accordance with the objects and practices of the present invention. It is intended, therefore, that the invention be defined by the scope of the claims which follow and that such claims be interpreted as broadly as is reasonable.

What we claim is:

1. An apparatus for the synthesis of chemical compounds comprising:
    a plurality of reaction vessels, wherein each of reaction vessels has an inner surface defining an interior, an outer surface, a first opening fluidly coupled to the interior, and a second opening fluidly coupled to the interior;
    a liquid circulation-inducing agitator element contained within the interior of each of said reaction vessels;
    a common manifold comprising:
        a fluid-sealing boss passing into the first opening of each said reaction vessel and forming an air tight seal;
        a common gas line having a gas outlet port formed in each said boss and fluidly coupled directly to the interior of each said reaction vessel;
        a common liquid line having a liquid outlet port formed in each said boss and fluidly coupled to the interior of each said reaction vessel; and
        an access passage passing through each said boss, each of said passages having an access passage inlet and an access passage outlet, where each access passage outlet is fluidly coupled to the interior of one of said reaction vessels, each access passage inlet opening on an outer surface of the manifold to allow materials to be added into selected ones of the reaction vessels;
    a valve fluidly coupled to the second opening of each said vessel.

2. An apparatus as in claim 1 further comprising:
    a support structure;
    the common manifold coupled to the support structure; and
    a valve manifold coupled to the support structure and containing said valves.

3. An apparatus as in claim 1 further comprising a sealing device for closing the access passage inlet of at least one said passage.

4. An apparatus as in claim 1 wherein each said passage has a cross-sectional area greater at its access passage inlet than at its access passage outlet.

5. An apparatus as in claim 2 wherein the common manifold is removably coupled to said plurality of reaction vessels and further comprising:
    a sliding device attached to the common manifold for moving manifold between a first position and a second position; and
    a locking device for securing the common manifold at least one of said first and second positions.

6. An apparatus as in claim 5 further comprising a hand grip attached to the common manifold to allow the user to exert a force on said manifold by hand.

7. An apparatus as in claim 2 wherein said valve manifold has valve control means for actuating each of said valves simultaneously.

8. An apparatus as in claim 1 wherein each of said valves has a liquid passageway and said passageway is covered with a chemically inert material.

9. An apparatus as in claim 8 wherein said chemically inert material is selected from the group comprising fluoropolymer and fluorinated ethylene-propylene.

10. An apparatus as in claim 1 wherein each of said valves comprises a flow control member made of a chemically inert material.

11. An apparatus as in claim 2 further comprising a heat exchanger coupled to the support structure and in heat transfer relationship with the reaction vessels, and wherein said heat exchanger contacts the outer surface of each of the reaction vessels.

12. An apparatus as in claim 11 wherein said heat exchanger contains a heating element and a cooling element.

13. An apparatus as in claim 11 wherein said heat exchanger comprises a polyimide film heater.

14. An apparatus as in claim 11 wherein said heat exchanger generates an evenly distributed area of heating having a maximum temperature variance of about 4 degrees C. between all of said reaction vessels at one point in time.

15. An apparatus as in claim 11 wherein said heat exchanger has a plurality of fittings for releasably coupling the reaction vessels to said heat exchanger.

16. An apparatus as in claim 1 further comprising a gas source coupled to said common gas line and a liquid source coupled to said common liquid line.

17. The apparatus of claim 1 wherein the reaction vessel is comprised of an inert material selected from the group consisting of: fluoropolymer, fluorinated ethylene-propylene, glass, propylene, polyethylene, ceramic, stainless steel coated with fluorinated ethylene-propylene, and stainless steel coated with fluoropolymer.

18. The apparatus of claim 1 wherein the reaction vessel is fitted with a frit on the lower portion of the reaction vessel.

19. The apparatus of claim 1 wherein the agitator element has a shape that is selected from the group consisting of: a plunger, stir bar, ball, bead, column or disk.

20. The apparatus of claim 19 wherein the agitator element is coated with an inert material.

21. The apparatus of claim 1 wherein the agitator element is made from a magnetic material and is actuatable longitudinally along the inner surface of the reaction vessel by a magnet positioned externally to the reaction vessel.

22. The apparatus of claim 2 further comprising:
    a controller;
    a plurality of pressurized liquid containers coupled to said common liquid line;
    a plurality of liquid container valves fluidly coupled to the liquid containers and the common liquid line; and
    said controller regulating these plurality of valves to control the flow of liquids from said containers.

23. The apparatus of claim 7 further comprising a controller for activating said valve control means.

24. An apparatus for the synthesis of chemical compounds comprising:

a support structure;

first and second manifolds mounted on said structure, said first manifold slidably mounted on said structure;

a plurality of reaction vessels wherein each said vessel has an inner surface, an outer surface, a first opening coupled to said first manifold, and a second opening coupled to said second manifold, wherein said first manifold defines separate liquid and gas pathways through the first opening and into each of said reaction vessels from liquid and gas sources;

an agitator movable within each of said reaction vessels for stimulating liquid circulation;

said first manifold comprising a separate access passage for each said reaction vessel to permit introduction of a substance through selected ones of the access passages and into the reaction vessels through their first openings; and said gas pathways capable of providing positive gas pressure to each reaction vessel to prevent outside air from contaminating said interior of any reaction vessel when its access passage is open.

25. An apparatus as in claim 24 further comprising a reaction vessel heater having a plurality of fittings, each fitting defining a slot allowing an associated reaction vessel to be viewed during processing.

26. An apparatus as in claim 24 wherein:

said reaction vessels comprise first and second parallel, spaced-apart reaction vessels, and further comprising:

a reciprocating magnetic device moving along a path between and parallel to said first and second reaction vessels to cause movement of said agitators therein.

27. An apparatus as in claim 24 wherein said second manifold comprises a plurality of valves defined by a single layer of material selected from the group comprising fluoropolymer and fluorinated ethylene-propylene.

28. An apparatus for the synthesis of chemical compounds comprising:

plurality of reaction vessels, wherein each of said reaction vessels has an inner surface defining an interior, an outer surface, a first opening fluidly coupled to the interior, and a second opening fluidly coupled to the interior;

a monolithic support structure supporting said reaction vessels;

a liquid circulation-inducing agitator element contained within the interior of each of said reaction vessels;

a common manifold coupled to the support structure and defining a common gas line bore and a common liquid line bore, the common manifold comprising a series of gas outlet ports and liquid outlet ports fluidly coupling the interior of each said reaction vessel with said common gas line bore and said common liquid line bore, respectively; and a valve fluidly coupled to the second opening of each said vessel.

29. An apparatus as in claim 28 further comprising:

a heat exchanger coupled to the support structure in heat transfer relationship with said reaction vessels.

30. An apparatus as in claim 28 wherein the common manifold has a plurality of access passages passing therethrough and through the first openings, each of said passages having an access passage inlet and an access passage outlet, where each access passage outlet is fluidly coupled to the interior of one of said reaction vessels, each access passage inlet opening on an outer surface of the manifold to allow materials to be added into the reaction vessel.

31. An apparatus as in claim 28 wherein said common manifold comprises a boss which extends through the first opening of each said reaction vessel, said liquid and gas outlet ports extending through said boss.

* * * * *